United States Patent
Nagel et al.

(10) Patent No.: US 8,710,078 B2
(45) Date of Patent: Apr. 29, 2014

(54) CRYSTALLINE SOLVATES OF 6-(PIPERIDIN-4-YLOXY)-2H-ISOQUINOLIN-1-ONE HYDROCHLORIDE

(75) Inventors: Norbert Nagel, Frankfurt am Main (DE); Bruno Baumgartner, Frankfurt am Main (DE); Harald Berchtold, Frankfurt am Main (DE); Oliver Plettenburg, Frankfurt am Main (DE); Dieter Kadereit, Frankfurt (DE); Mandy Mohnicke, Frankfurt am Main (DE); Simon Gessler, Frankfurt am Main (DE); Joachim Tillner, Frankfurt (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/534,815

(22) Filed: Jun. 27, 2012

(65) Prior Publication Data

US 2013/0012444 A1 Jan. 10, 2013

(30) Foreign Application Priority Data

Jul. 8, 2011 (EP) .................. 11305890
Dec. 29, 2011 (EP) .................. 11306033

(51) Int. Cl.
*C07D 401/12* (2006.01)
*A61K 31/4725* (2006.01)

(52) U.S. Cl.
CPC .......... *C07D 401/12* (2013.01); *A61K 31/4725* (2013.01)
USPC ......................... 514/309; 546/141

(58) Field of Classification Search
None
See application file for complete search history.

(56) References Cited

FOREIGN PATENT DOCUMENTS

| WO | WO2007/012421 A1 | 2/2007 |
| WO | WO2008/077550 A1 | 7/2008 |
| WO | WO2009/080335 A1 | 7/2009 |

OTHER PUBLICATIONS

Morissette et al, Advanced Drug Delivery Reviews, 56 (2004), pp. 275-300.*
West, Anthony R., Solid State Chemistry and its Applications, Wiley, New York, 1988, pp. 358 & 365.*
Caira, Mino R., "Crystalline Polymorphism of Organic Compounds," Topics in Current Chemistry (1998), vol. 198, pp. 163-208.
Ray, Peter et al., "Optimisation of 6-substituted isoquinolin-1-amine based ROCK-1 inhibitors," Bioorganic and Medicinal Chemistry Letters (2011), vol. 21, 1084-1088.
European Search Report dated Oct. 11, 2011 issued in EP11305890.
European Search Report dated Feb. 3, 2012 issued in EP11306033.
International Search Report dated Aug. 7, 2012 issued in PCT/EP2012/062431.

* cited by examiner

*Primary Examiner* — Zinna Northington Davis
(74) *Attorney, Agent, or Firm* — Scully, Scott, Murphy & Presser, P.C.

(57) ABSTRACT

The present invention relates to crystalline solvates of 6-(Piperidin-4-yloxy)-2H-isoquinolin-1-one hydrochloride, processes for their preparation and the use thereof.

21 Claims, 14 Drawing Sheets

CRYSTALLINE SOLVATES OF 6-(PIPERIDIN-4-YLOXY)-2H-ISOQUINOLIN-1-ONE HYDROCHLORIDE

The present invention relates to new crystalline solvates of 6-(Piperidin-4-yloxy)-2H-isoquinolin-1-one hydrochloride, processes for their preparation and their use, in particular for the preparation of medicaments.

6-(Piperidin-4-yloxy)-2H-isoquinolin-1-one is known as a pharmaceutically active compound. 6-(Piperidin-4-yloxy)-2H-isoquinolin-1-one is described as free base in WO 2007/065916. WO2007/012421, WO2008/077550 and WO 2009/080335 describe the synthesis of 6-(Piperidin-4-yloxy)-2H-isoquinolin-1-one and its hydrochloride but do not contain any evidence of a controlled, reproducible crystallisation procedure. The described material is only obtained by lyophilisation.

The hydrochloric acid (HCl) salt of 6-(Piperidin-4-yloxy)-2H-isoquinolin-1-one is the compound of formula (I)

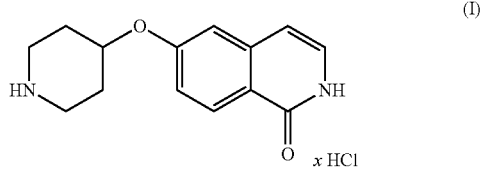 [SMILES: O=c1[nH]ccc2cc(OC3CCNCC3)ccc12]

(I)

The compound of formula (I) can also exist in its tautomeric form as 1-hydroxy-isoquinoline and this tautomer is a further embodiment of the present invention.

Solvates are compounds formed by solvation, which is the combination of solvent molecules with molecules or ions of the solute. Solvation is an interaction of a solute with the solvent, which leads to stabilization of the solute species in the solution. One may also refer to the solvated state, whereby an ion in a solution is complexed by solvent molecules. The solvent does the dissolving. Solvents can be gases, liquids, or solids. If the solvent is a solid, then gases, liquids, and solids can be dissolved. Examples for liquid in solid are e.g. mercury in gold, forming an amalgam. Solvates and especially solid solvates may have different and distinct physical properties, such as different solubility profiles, different thermodynamic stability, different crystallization behavior, different filterability, different melting point temperatures and/or different X-ray diffraction peaks. The difference in the physical properties of different solvates and polymorphic forms thereof results from different orientation and intermolecular interactions of adjacent molecules in the solid. Polymorphic forms of compounds or solvates can be distinguished by X-ray diffraction and by other methods such as, infrared spectroscopy or Raman spectroscopy, for example.

A hydrate is a solvate containing water. According to the invention the term of a hydrate of compound (I) includes all aqueous solvates of compound (I) where water is present in any ratio to compound (I).

However, as acknowledged by the person skilled in the art, the presence of new solid solvates of a known chemical compound cannot be foreseen. The existence of crystalline phases (hydrates or solvates) cannot be foreseen. Also the conditions under which crystallization takes place to give a specific form, and the characteristics of the polymorphic forms and solvates cannot be predicted. Since properties such as the solubility and stability and consequently the suitability for use and storage of each polymorph and solvate may vary, identifying the existence of polymorphs is essential for providing pharmaceuticals with increased storage stability or predictable solubility profiles.

It was the object of the present invention to provide new solid forms of 6-(Piperidin-4-yloxy)-2H-isoquinolin-1-one hydrochloride (compound (I)). In particular it was the objective to provide new crystalline solid forms of compound (I). In particular it was the objective to provide new crystalline solid forms of compound (I), which have a favorable property profile or are useful in the preparation of the compound. In particular it was the objective to provide new crystalline solid forms of compound (I), which have such favorable properties, which make the use of compound (I) as a pharmaceutically active compound more favorable.

In particular it was the objective to provide new crystalline solid forms of compound (I), which have favorable properties with respect to stability, solubility, processability, hygroscopicity, flowability, filterability or crystallization rate.

The objectives of the invention are met by the following embodiments.

An embodiment of the present invention relates to a hydrate of 6-(Piperidin-4-yloxy)-2H-isoquinolin-1-one hydrochloride. In one embodiment the hydrate is a dihydrate. Another embodiment of the present invention relates to 6-(Piperidin-4-yloxy)-2H-isoquinolin-1-one hydrochloride dihydrate and polymorph 2 and any mixture thereof. A further embodiment of the present invention relates to a solvate of compound (I) with an organic solvent, especially a solvate selected from a methyl acetate solvate, a 1,4-dioxane solvate or an acetonitrile solvate.

In the context of the present invention, polymorph, polymorphic form, solvate etc. always refers to a polymorph, polymorphic form or solvate of 6-(Piperidin-4-yloxy)-2H-isoquinolin-1-one hydrochloride. The terms "polymorph", "form" and "phase" may be used interchangeably herein. The anhydrous and solvent free forms as well as the hydrates and organic solvates of the present invention were obtained as outlined in the Examples provided below.

Hydrate

One embodiment the present invention is a crystalline hydrate of 6-(Piperidin-4-yloxy)-2H-isoquinolin-1-one hydrochloride (I). Another embodiment the present invention is a crystalline hydrate of compound (I) wherein the hydrate contains about 10.5-12.5% water (w/w). Another embodiment of the present invention is a hydrate wherein the hydrate contains 1.85-2.2 molecules water per molecule 6-(Piperidin-4-yloxy)-2H-isoquinolin-1-one hydrochloride (I). Another embodiment of the present invention is a hydrate wherein the hydrate contains 2 molecules water per molecule 6-(Piperidin-4-yloxy)-2H-isoquinolin-1-one hydrochloride (I).

A crystalline hydrate containing 1.85-2.2 molecules water per molecule is herein referred to as "dihydrate" and is an embodiment of the present invention.

In another embodiment of the hydrate the water content is 10.5-11.4% water (w/w). In a further embodiment the hydrate contains about 1.85-2.0 molecules water.

In a further embodiment of the hydrate the water content is 11.4% (w/w). in a further embodiment the hydrate contains 2.0 molecules water per molecule (I).

Although the hydrate phase typically contains about 10-12.5% water it can also occur with lower water content. The crystal structure of the hydrate remains even if the dihydrate is dried and the remaining water content is down to about 3%. Water uptake is reversible if humidity in the environment is raised again. The water content in the isolated product depends on the drying conditions used during work up of the hydrate after crystallisation.

In one embodiment the dihydrate has the property of having at least a characteristic reflection in an X-ray powder diffractogram using CuK$\alpha_1$ radiation at 7.7±0.2 degrees 2theta.

In another embodiment the dihydrate has the property of having at least characteristic reflections in an X-ray powder diffractogram using CuK$\alpha_1$ radiation at 7.7 (strong), 15.2 (strong) and 16.8 (medium) degrees 2theta±0.2 degrees 2theta.

In another embodiment the dihydrate has the property of having at least characteristic reflections in an X-ray powder diffractogram using CuK$\alpha_1$ radiation at 7.7 (strong), 15.2 (strong), 16.8 (medium), 22.4 (strong), 25.0 (strong) and 26.6 (strong) degrees 2theta±0.2 degrees 2theta.

In another embodiment the dihydrate has the property of having at least characteristic reflections in an X-ray powder diffractogram using CuK$\alpha_1$ radiation at 7.7 (strong), 15.2 (strong), 16.8 (medium), 18.4 (medium), 20.4 (medium), 22.4 (strong), 25.0 (strong), 26.6 (strong) and 30.3 (medium) degrees 2theta±0.2 degrees 2theta.

Figure 1:
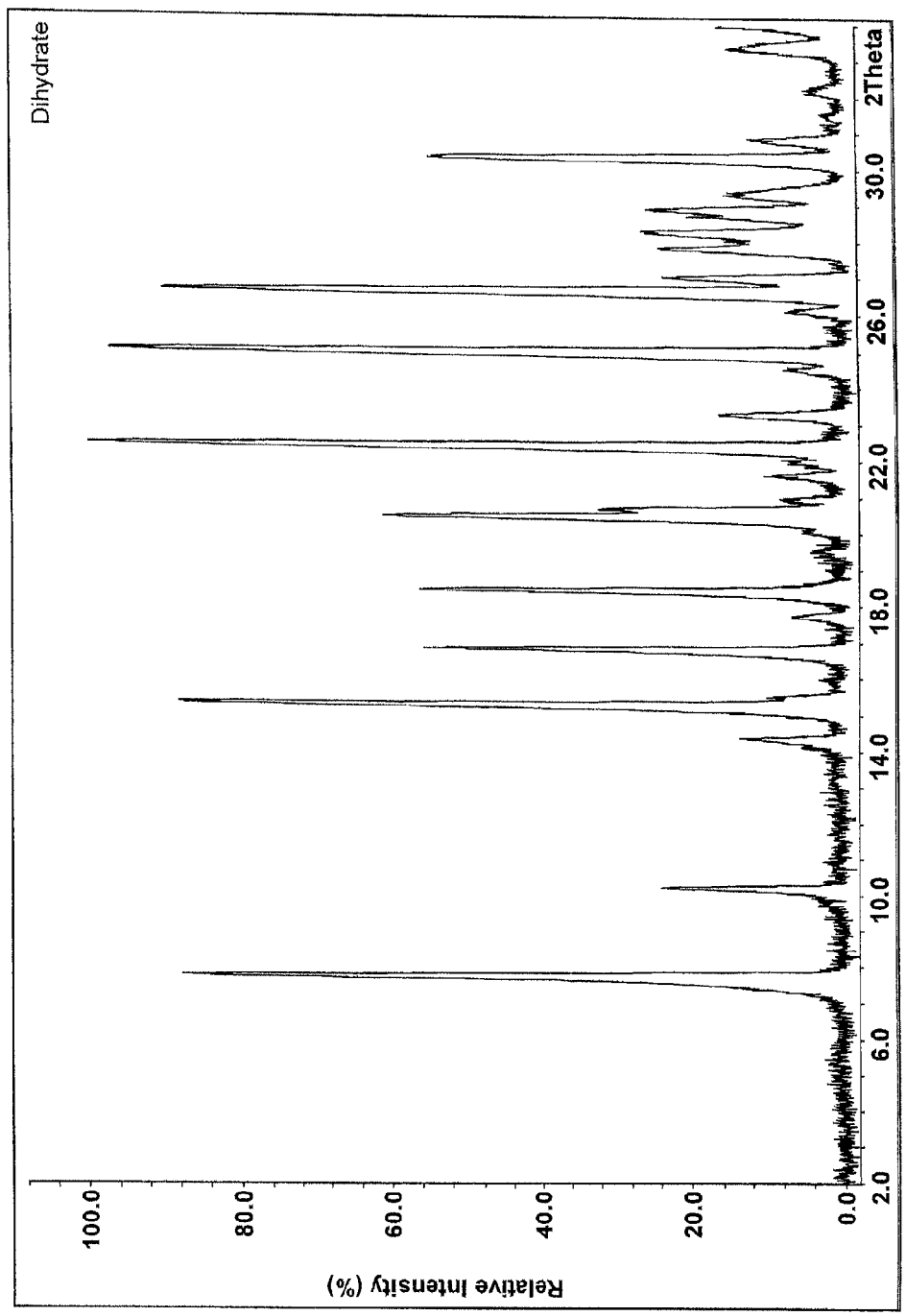
FIG. 1—X-ray powder diffraction pattern of 6-(Piperidin-4-yloxy)-2H-isoquinolin-1-one hydrochloride dihydrate, measured in transmission mode with CuK$\alpha_1$ radiation at room temperature (x-axis: diffraction angle 2theta (2θ) [°]; y-axis: relative intensity [% of the highest reflection]).

In another embodiment the dihydrate may also be characterized by its X-ray powder diffraction pattern substantially by the one shown in FIG. 1, which has been obtained using CuK$\alpha_1$ radiation in transmission mode, wherein the intensities of the reflections depicted in the Figure as well as those of the reflections specified above are not a prerequisite, but may vary.

The dihydrate may also be characterized by its crystal parameters which have been determined by single crystal structure analysis.

It was found that the dihydrate crystallizes in the space group P-1, Z=2 with one molecule (I) and two molecules of water in the asymmetric unit.

The measured data of the unit cell are given in Table 1.

TABLE 1

Unit cell parameters of the dihydrate of compound (I) at room temperature

| Phase | Dihydrate |
| --- | --- |
| Crystal system | triclinic |
| Space group | P-1; Z = 2 |
| Summation formula | $C_{14}H_{21}ClN_2O_4$ |
| Cell dimensions | a = 6.904 Å |
|  | b = 9.907 Å |
|  | c = 12.256 Å |
|  | α = 107.60° |
|  | β = 96.70° |
|  | γ = 102.73° |
| Cell volume V (1) | 764 Å$^3$ |
| Density ρ (1) | 1.377 Mg/m$^3$ |

(1) calculated

The crystal water molecules are located in channels parallel to the crystallographic axis and the water molecules form hydrogen bonds to the chloride anion as well as to the molecular cation.

Figure 2:
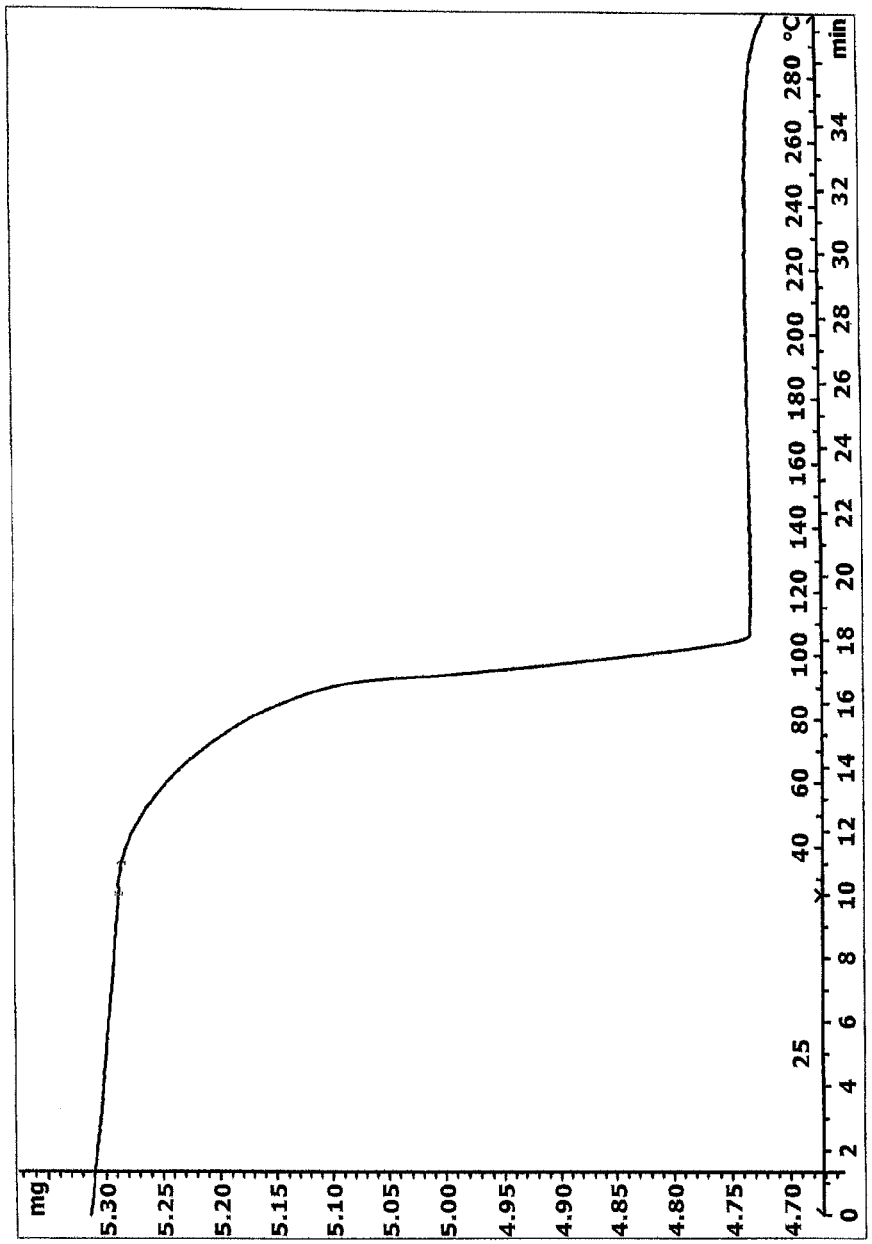
FIG. 2—TGA Thermogram of the dihydrate of compound (I).

The dihydrate may also be characterized by its TGA diagram as shown in FIG. 2. On heating the dihydrate in a dry environment, a significant weight loss starts already at slightly elevated temperature and ends at about 110° C. In this example the diagram shows a weight loss of 0.57 mg water corresponding to 10.8 mass-% water, which means that this sample lost about 1.9 mol water per mol compound (I) on heating.

The water content in the dihydrate may also be determined by other methods known in the art such as Karl-Fischer titration.

Figure 3:
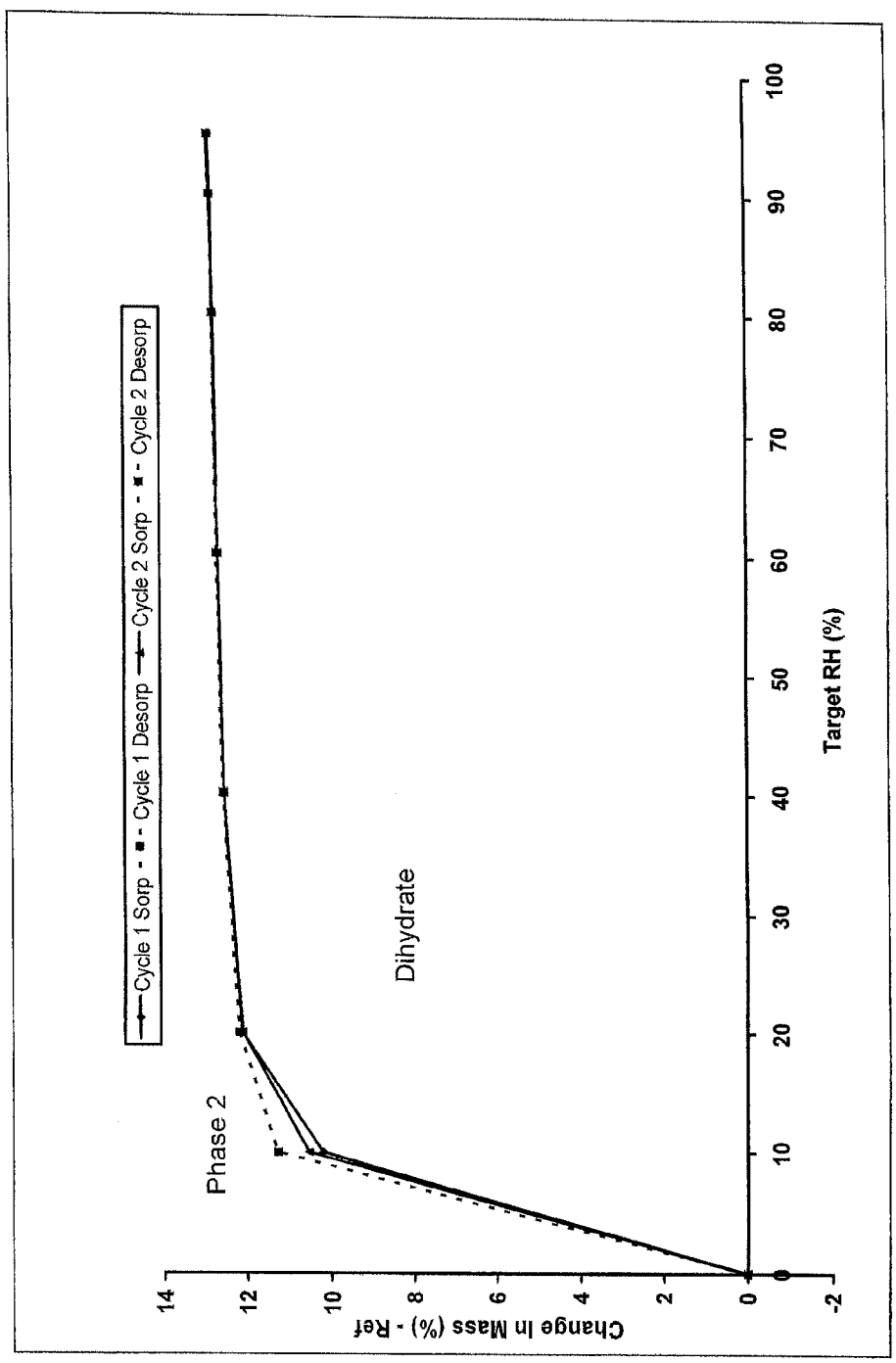
FIG. 3—DVS Phase transitions and water content as a function of relative humidity (25-40° C.) of the dihydrate which, due to a drying period at the beginning before starting the first sorption cycle, had converted into Phase 2.

Moreover, the dihydrate may also be characterized by its DVS (dynamic vapor sorption) water vapor sorption and desorption isotherms measured at 25° C. as shown in FIG. 3. Before starting the sorption cycle the dihydrate probe is treated with dry nitrogen gas resulting in a transformation into phase 2 as shown by humidity resolved XRPD. As shown in FIG. 3, the sorption and desorption isotherms are almost the same. In the sorption cycle the water content of the probe quickly increases when phase 2 is exposed to relative humidities between 1 and 20% and remains almost constant between 20 and 95%. In the desorption cycle the water content remains almost constant when the dihydrate is exposed to relative humidities between 95% and 20%. A weight loss starts below 20% relative humidity and becomes strong below 10%, especially below 5%. The change in mass at low relative humidity is completely reversible and when the humidity increases again, the rehydration proceeds rapidly with small samples. However, for bulk samples rehydration of over-dried samples can take considerably longer and rehydration may require several days. Almost identical water sorption and desorption isotherms are observed at 40° C.

Depending on the environment and storage conditions of the dihydrate, especially if humidity is below about 10%, especially below about 5%, the dihydrate may partly or completely transform into polymorph 2. The degree of conversion depends on humidity, sample size and length of exposure to a dry environment. Thus in a further embodiment the invention relates to the dihydrate comprising an amount of polymorph 2 in a range from 1% to 99%, especially in a range from 1 to 10%. For definition purposes any amount of another polymorph is calculated relative to the amount of dihydrate.

XRPD analysis in a humidity chamber revealed that at rather low relative humidity (2%) and when the sample is almost completely dehydrated, a transformation to phase 2 takes place. For the measurement, the relative humidity (r.h.) in the chamber was first linearly lowered from 50% to 2% in 6 hours, held at 2% for 6 hours, then cycled twice between 2% and 95% for 6 hours (holding the sample at 95% and 2% for 6 hours), and finally increased to 50% during 7 hours. A reversible transformation for the hydrate into phase 2 was observed at 2% r.h., the back transformation into the dihydrate is taking place between 8 and 10% r.h.

When humidity-controlled XRPD was performed at 25 and 40° C., widely identical results were obtained.

On the other hand, temperature-resolved XRPD shows that this loss of water is accompanied or followed by the transformation to phase 3, whose transformation starts to take place at about 90° C.

Based on these findings the dihydrate is stable below 90° C. and thus also at room temperature. Therefore, in comparison to the other described anhydrous polymorphs, the dihydrate is particularly suitable when a high stability is desired. It is the only one that can be stored at relative humidities between 20 and 95% in different environments below 90° C., which are usual storage conditions, without the risk of transformation into another described crystalline phase. Even if exposed to a very dry environment, a possible water loss is reversible and the missing water is gained back once the compound is back in an environment having usual humidity conditions. Therefore, the dihydrate is in particular suitable for the preparation of medicaments and pharmaceutical compositions with improved stability.

Moreover, the corresponding amorphous material is hygroscopic and the water content varies much stronger with the relative humidity compared to the dihydrate. This water uptake and variability in water content makes precise dosing during drug product manufacturing difficult. In contrast, the dihydrate has been proven to be stable for more than two years under usual storage conditions (no detectable decomposition at 25° C./65% relative humidity). Accordingly, the crystalline dihydrate is therefore the preferred solid form for drug product manufacturing.

Figure 13:
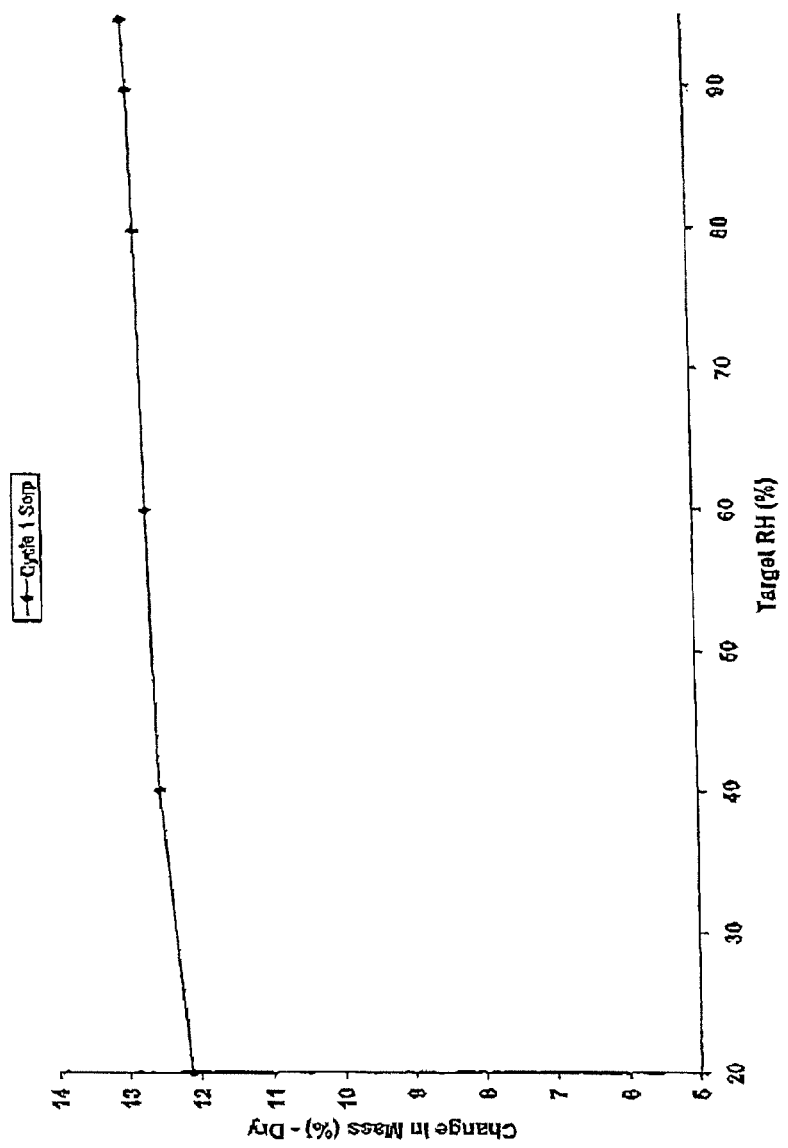
FIG. 13—DVS water vapour sorption as a function of relative humidity of the dihydrate at 25° C.
Figure 14:
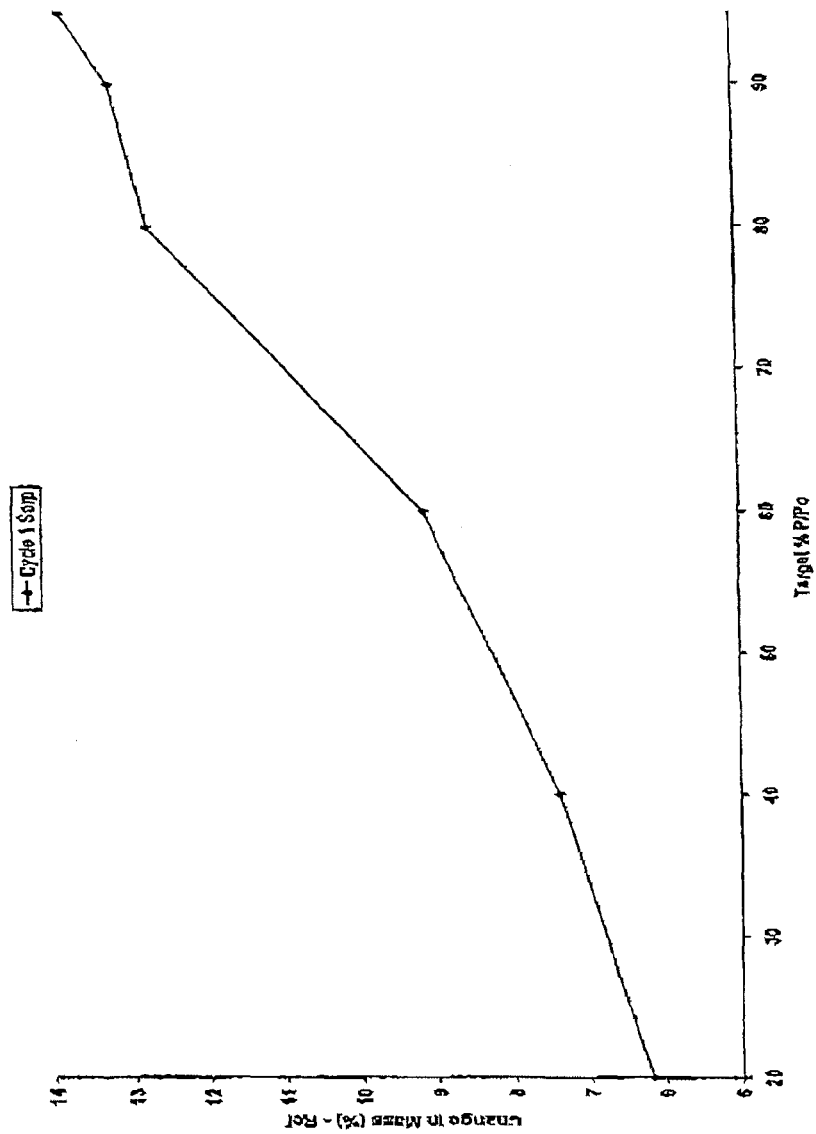
FIG. 14—DVS water vapour sorption as a function of relative humidity of the amorphous form of compound (I) at 25° C. for purpose of comparison to the dihydrate.

Furthermore, the dihydrate may also be characterized by its DVS (dynamic vapor sorption) water vapor sorption and desorption isotherms measured at 25° C. as shown in FIG. 13. Like that, a comparison to the characterization of the amorphous compound (I) by its DVS (dynamic vapor sorption) water vapor sorption and desorption isotherms measured at 25° C. shown in FIG. 14 is possible. The dihydrate surprisingly and unexpectedly belongs to the rare class of stoichiometric hydrates, i.e. the dihydrate maintains a quite constant water content when exposed to a broad range of relative humidities. This property is advantageous for example when the active pharmaceutical ingredient is dried after crystallization or weighed during manufacturing of the dosage form as well as during storage of the solid dosage form.

As already mentioned the amorphous material is hygroscopic and adjusts its water content to the ambient relative humidity (FIG. 13). A stable (molecular) weight of this material is only reached, if by chance the water content corresponds to the equilibrium water content at the ambient relative humidity, to which the sample is exposed. Moreover many key properties of the amorphous material change with its water content, such as molecular mobility, dissolution rate and the tendency to transform into other solid phases. Thus, the hygroscopic amorphous material has to be regarded as unfavourable for oral solid dosage forms. Unexpectedly the closely related dihydrate is suitable as a solid for drug product manufacturing due to its favourable properties and stability.

Polymorph 2

Another aspect of the present invention relates to polymorph 2 of compound (I) which has the property of having at least characteristic reflections in an X-ray powder diffractogram using CuK$\alpha_1$ radiation at
8.1 (medium),
15.8 (strong) and
16.5 (medium) degrees 2theta±0.2 degrees 2theta.

In another aspect the polymorph has the property of having at least characteristic reflections in an X-ray powder diffractogram using CuK$\alpha_1$ radiation at
8.1 (Medium), 15.8 (Strong), 16.5 (Medium), 17.7 (Medium), 19.6 (Medium),
20.8 (Medium), 22.2 (medium), 25.0 (Medium), 26.6 (Medium) and
30.5 (Medium) degrees 2theta±0.2 degrees 2theta.

Figure 4:
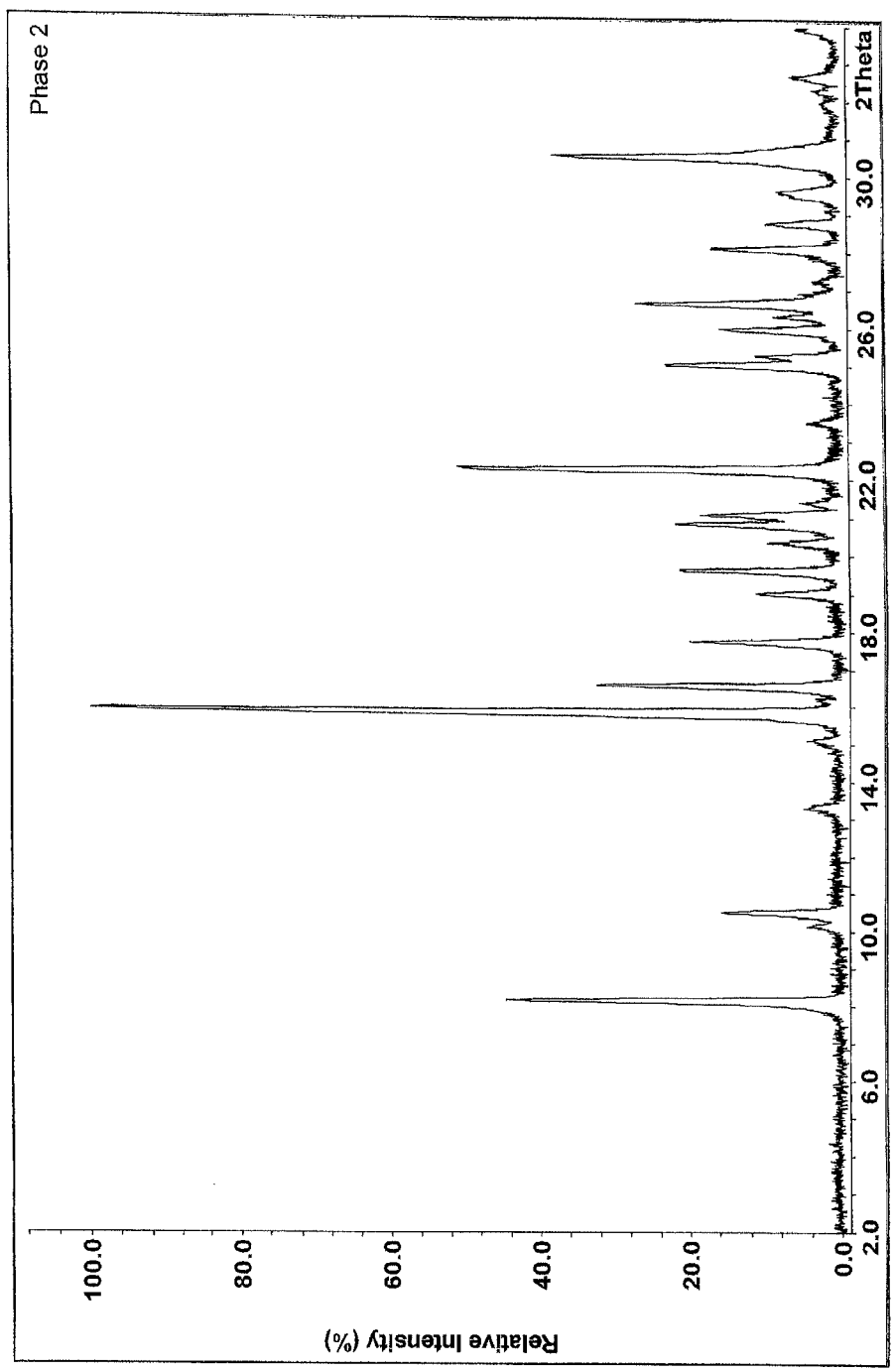
FIG. 4—X-ray powder diffraction pattern of polymorph 2 of compound (I), measured in transmission mode with CuK$\alpha_1$ radiation at room temperature (x-axis: diffraction angle 2theta (2θ) [°]; y-axis: relative intensity [% of the strongest reflection]).

In another embodiment polymorph 2 may also be characterized by its X-ray powder diffraction pattern substantially as the one shown in FIG. 4.

This has been obtained using CuK$\alpha_1$ radiation in transmission mode, wherein the intensities of the reflections depicted in the Figure as well as those of the reflections specified above are not a prerequisite, but may vary.

Polymorph 2 may also be characterized by its DVS water vapor sorption, wherein it transforms into the dihydrate, and desorption isotherms, where it transforms back into form 2. For further details see description of the dihydrate and FIG. 3.

Polymorph 2 is not obtained directly on crystallization from solution. It typically forms at ambient temperature or at 40° C., when the dihydrate is exposed to a rather low relative humidity (preferably less than 5%, more preferably less than 2%) and transforms back to the dihydrate when polymorph 2 is exposed to increasing humidity preferably at a relative humidity above about 10%. Accordingly, polymorph 2 is especially useful if the dihydrate should be obtained.

Depending on the environment and storage conditions of polymorph 2, especially if humidity is increased above about 10%, polymorph 2 partly or completely transforms into the dihydrate and thus the sample may comprise the dihydrate in a range from 0.1% to 100%.

In a further aspect the invention relates to polymorphs 1, 3 and 4 of compound (I), which unlike polymorph 2, can be directly obtained from compound (I) and which then can also be converted into the dihydrate.

In one aspect the three anhydrous polymorphs are characterized by exhibiting in an X-ray powder diffractogram using CuKα$_1$ radiation at least characteristic reflections at
1) 15.4 degrees 2theta and within each of the ranges selected from
2) 16.6-16.8 and
3) 21.5-21.7 degrees 2theta±0.2 degrees 2theta.

Polymorph 1

Another aspect of the present invention relates to polymorph 1 of 6-(Piperidin-4-yloxy)-2H-isoquinolin-1-one hydrochloride which has at least
characteristic reflections in an X-ray powder diffractogram (XRPD) using CuKα$_1$ radiation at
4.5 (medium),
15.4 (strong),
16.8 (strong),
21.7 (medium) and
24.7 (medium) degrees 2theta±0.2 degrees 2theta.

In another aspect polymorph 1 has the property of having at least characteristic reflections in an X-ray powder diffractogram using CuKα$_1$ radiation at
4.5 (medium), 15.4 (strong), 16.8 (strong), 19.8 (weak), 21.7 (medium),
22.5 (strong), 22.8 (Strong), 24.7 (medium) and
27.3 (medium) degrees 2theta±0.2 degrees 2theta.

Figure 5:
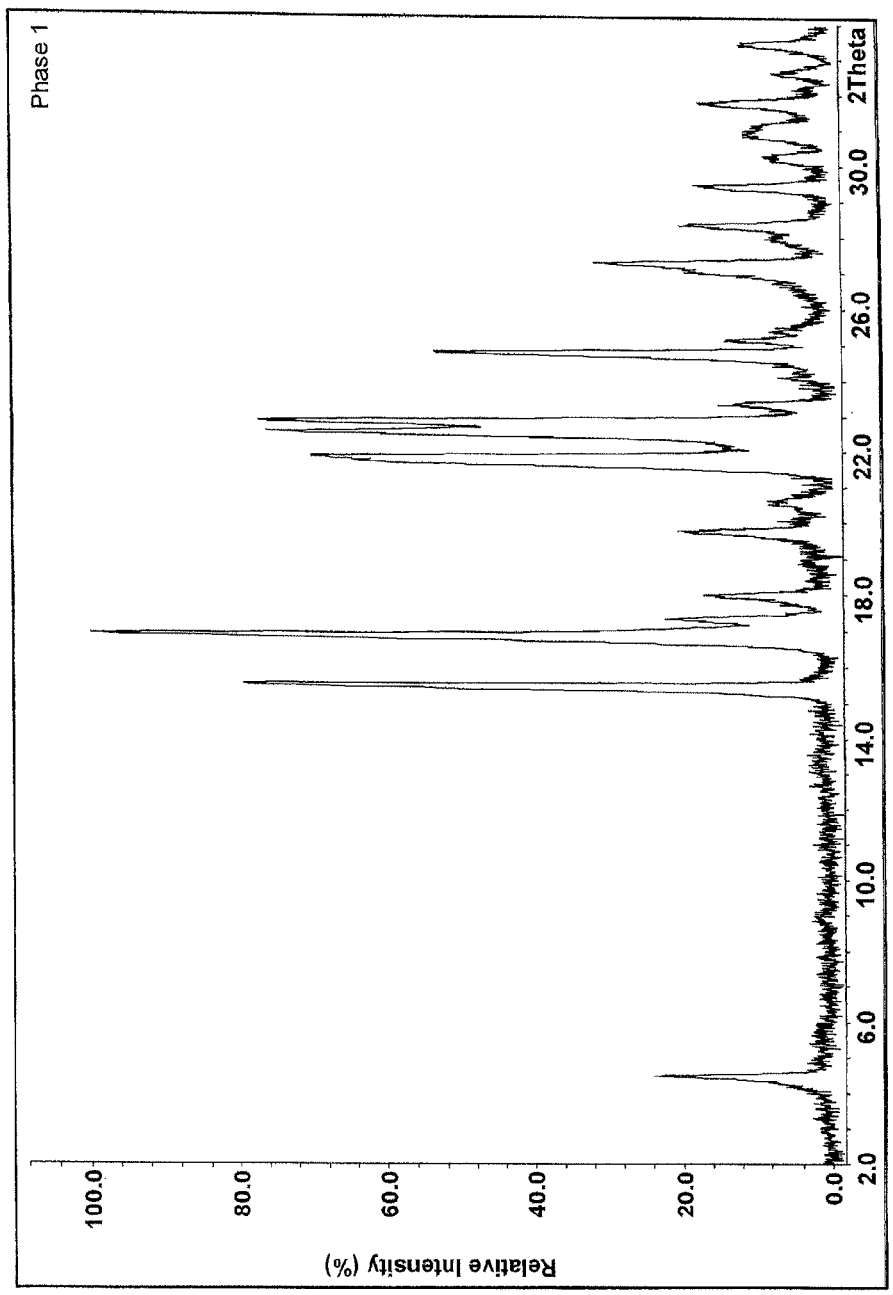
FIG. 5—X-ray powder diffraction pattern of polymorph 1 of compound (I), measured in transmission mode with CuK$\alpha_1$ radiation at room temperature (x-axis: diffraction angle 2theta (2θ) [°]; y-axis: relative intensity [% of the strongest reflection]).

In another embodiment polymorph 1 may also be characterized by its X-ray powder diffraction pattern such as the one shown in FIG. 5.

This has been obtained using CuKα$_1$ radiation in transmission mode, wherein the intensities of the reflections depicted in the Figure as well as those of the reflections specified above are not a prerequisite, but may vary.

Polymorph 1 may also be characterized by its melting characteristics such as its melting point with a DSC. On heating, phase 1 starts to melt at about 300° C., preceded and accompanied by chemical decomposition. No transformation into another crystalline phase is observed prior to melting.

Exposure to elevated humidity causes transformation to the dihydrate as determined with humidity-controlled XRPD performed at 25° C. The relative humidity in the chamber was first held at 2% for 6 hours, then linearly increased to 95% during 19 hours, held at 95% for 6 hours, linearly decreased to 2% for 19 hours and held at 2% for another 10 hours. Phase 1 transformed into the dihydrate after about 15 min at 95%, which in turn changed to phase 2 after about 40 min at 2% r.h.

Also storage of phase 1 at 20° C. and 75% relative humidity caused complete conversion to the dihydrate within 3 weeks. The rate of conversion correlates with the relative humidity.

Maturation experiments with suspensions starting from phase mixtures (see maturation experiments) indicate that in the temperature range from 0 to 40° C. phase 1 is only a metastable polymorph.

Polymorph 1 may thus be used in the preparation of the dihydrate and further in the preparation of polymorph 2.

Polymorph 3

Another aspect of the present invention relates to polymorph 3 of 6-(Piperidin-4-yloxy)-2H-isoquinolin-1-one hydrochloride which has the property of having at least characteristic reflections in an X-ray powder diffractogram using CuKα$_1$ radiation at
4.5 (medium),
15.4 (strong),
16.7 (strong),
21.7 (strong) and
25.5 (medium) degrees 2theta±0.2 degrees 2theta.

In another aspect polymorph 3 has the property of having characteristic reflections in an X-ray powder diffractogram using CuKα$_1$ radiation at
4.5 (medium), 15.4 (strong), 16.7 (strong), 21.7 (strong), 22.0 (medium),
22.3 (medium) and 25.5 (medium) degrees 2theta±0.2 degrees 2theta.

Figure 6:
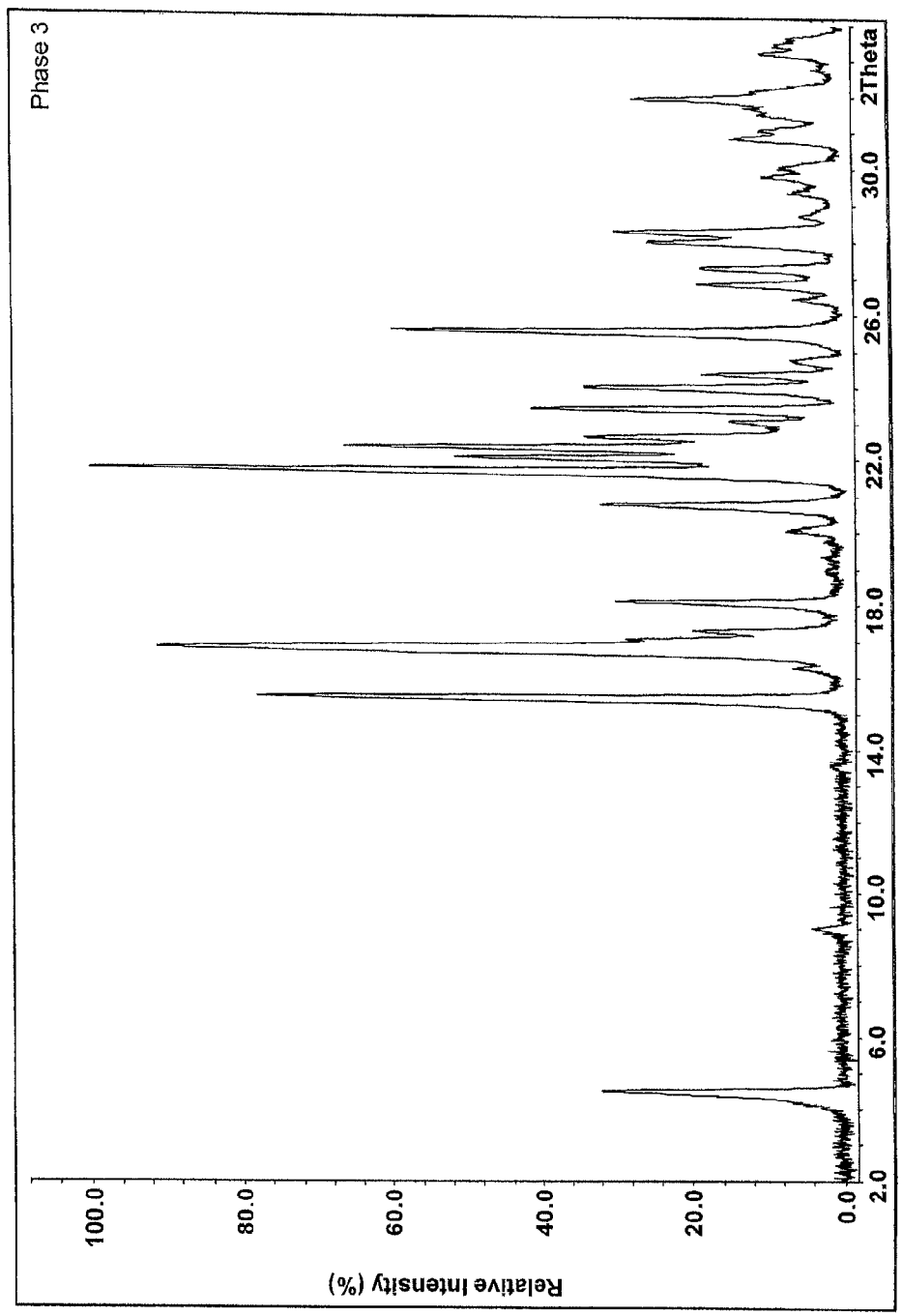
FIG. 6—X-ray powder diffraction pattern of polymorph 3 of compound (I), measured in transmission mode at room temperature with CuK$\alpha_1$ radiation (x-axis: diffraction angle 2theta (2θ) [°]; y-axis: relative intensity [% of the strongest reflection]).

Polymorph 3 may also be characterized by its X-ray powder diffraction pattern being substantially as the one shown in FIG. 6. This has been obtained using CuKα$_1$ radiation in transmission mode, wherein the intensities of the reflections depicted in the Figure as well as those of the reflections specified above are not a prerequisite, but may vary, and represent another embodiment of the invention.

Polymorph 3 may also be characterized by its melting characteristics such as its melting point with a DSC. On heating, phase 3 starts to melt at about 300° C., preceded and accompanied by chemical decomposition. No transformation into another crystalline phase is observed at low humidity prior to melting.

Exposure to elevated humidity causes transformation to the dihydrate as determined by humidity-controlled XRPD at 25° C. The relative humidity (r.h.) in the chamber was first linearly lowered from 50% to 2% in 6 hours, held at 2% for 6 hours, then linearly increased to 95% during 12 hours, held at 95% for 6 hours, linearly decreased to 2% in 12 hours and held at 2% for another 6 hours. As a result phase 3 transformed into the hydrate after about 30 min at 95%, which in turn changed to phase 2 after about 30 min at 2% r.h.

Figure 7:
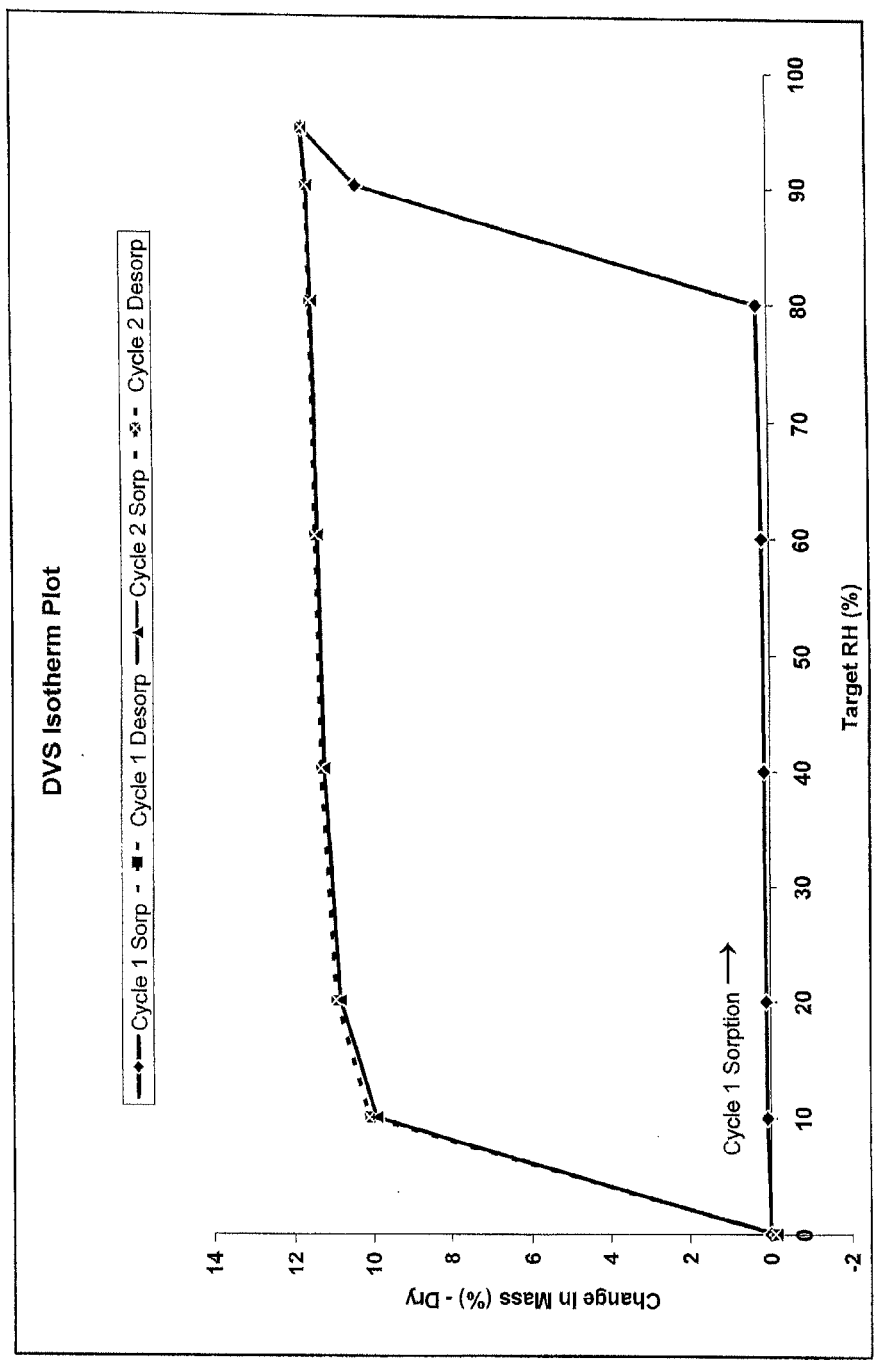
FIG. 7—Phase transitions and water content as a function of relative humidity at 25° C. starting with Phase 3 (as determined from DVS and humidity-resolved XRPD).

Moreover, phase 3 may also be characterized by its DVS (dynamic vapor sorption) water vapor sorption and desorption isotherms measured at 25° C. (FIG. 7)

The Figure shows in agreement with humidity controlled XRPD described before, that phase 3 remains with increasing humidity and changed into the dihydrate above about 80% relative humidity (cycle 1, sorption). With decreasing humidity the dihydrate converts back at low humidity (below about 10% r.h.) into phase 2 (cycle 1, desorption). Phase 2 then converts into the dihydrate with increasing humidity and along the same isotherm it converts back with decreasing humidity into polymorph 2 (cycle 2, see also FIG. 3)

The corresponding DVS Figures for the transformations of phase 1 and phase 4 into the dihydrate, which then converts back into phase 2 look similar.

Also storage of phase 3 at 20° C. and 75% relative humidity caused complete conversion to the dihydrate within 3 weeks. The rate of conversion correlates with the relative humidity. When suspended in water, complete transformation into the dihydrate was observed almost immediately (<10 min).

Moreover, maturation experiments with suspensions starting from phase mixtures in dry organic solvents (see Examples) indicate that in the temperature range from 0 to 40° C., phase 3 is the most stable anhydrous phase. These data show that polymorph 3 is at and around room temperature the most stable phase at low relative humidity (less than about 10% relative humidity).

Polymorph 3 can easily be obtained by crystallization from various water free solvents at elevated temperatures and is thus suitable for the isolation and purification of crude compound (I).

Polymorph 4

The present invention further relates to polymorph 4 of 6-(Piperidin-4-yloxy)-2H-isoquinolin-1-one hydrochloride which has the property of having at least characteristic reflections in an X-ray powder diffractogram using CuK$\alpha_1$ radiation at
15.4 (medium),
16.7 (medium),
21.5 (strong) and
30.7 (weak) degrees 2theta±0.2 degrees 2theta.

In another aspect polymorph 4 has the property of having at least characteristic reflections in an X-ray powder diffractogram using CuK$\alpha_1$ radiation at
15.4 (medium), 16.7 (medium), 16.9 (medium), 21.5 (strong), 21.9 (weak),
22.4 (medium), 23.2 (weak), 27.6 (weak) and 30.7 (weak) degrees 2theta±0.2 degrees 2theta.

Figure 8:
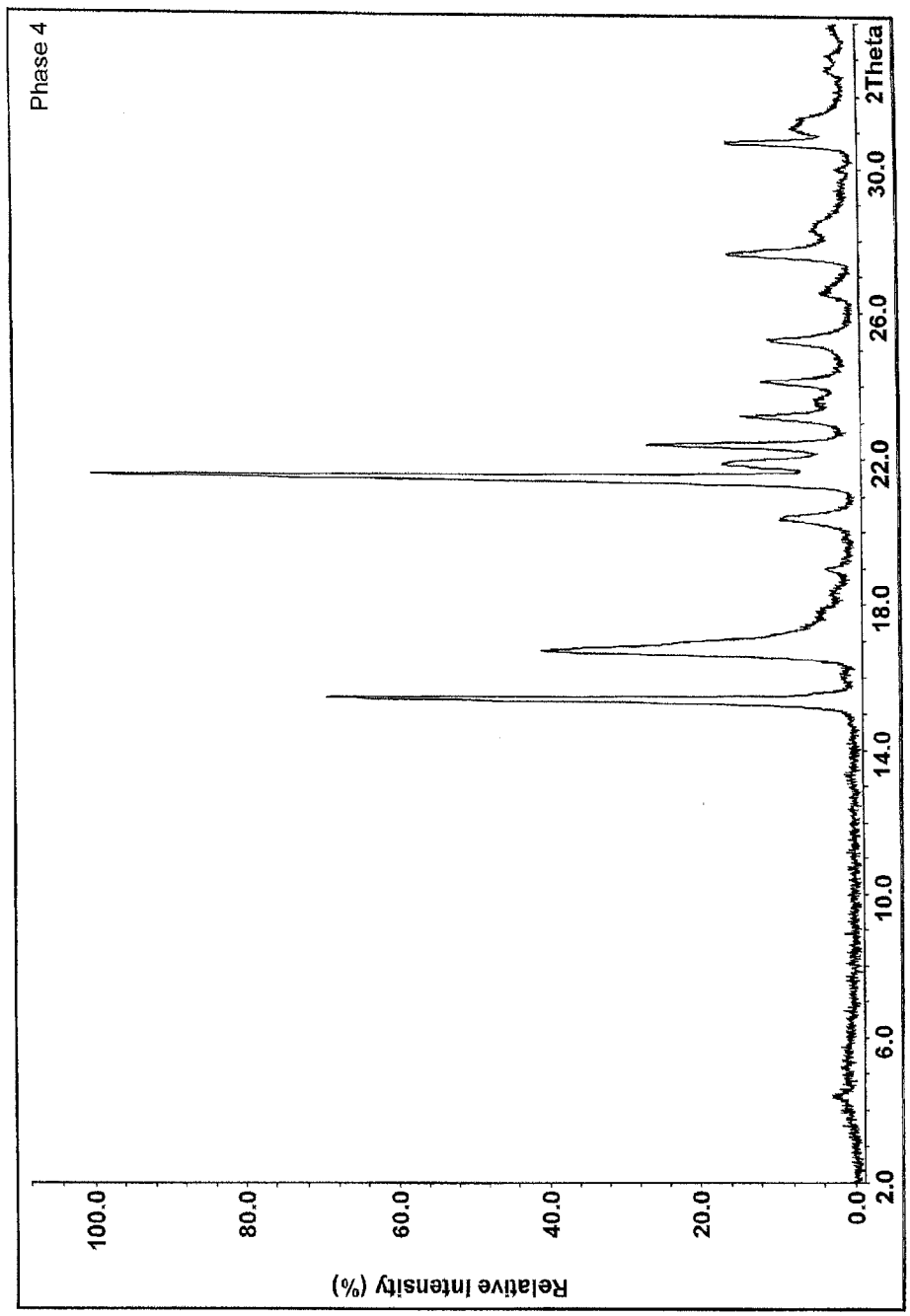
FIG. 8—X-ray powder diffraction pattern of polymorph 4 of compound (I), measured in transmission mode at room temperature with CuK$\alpha_1$ radiation (x-axis: diffraction angle 2theta (2θ) [°]; y-axis: relative intensity [% of the strongest reflection]).

In another embodiment polymorph 4 may also be characterized by its X-ray powder diffraction pattern such as the one shown in FIG. 8. This has been obtained using CuK$\alpha_1$ radiation in transmission mode, wherein the intensities of the reflections depicted in the Figure as well as those of the reflections specified above are not a prerequisite, but may vary.

Polymorph 4 may also be characterized by its melting characteristics such as its melting point determined with DSC (differential scanning calorimetry).

On heating, phase 4 starts to melt at about 300° C., preceded and accompanied by chemical decomposition. No transformation into another crystalline phase 1, 2 or 3 is observed prior to melting.

Exposure to elevated humidity causes transformation to the dihydrate as determined by humidity-controlled XRPD. First humidity was linearly lowered from 50% to 2% in 6 hours, held at 2% for 6 hours, then linearly increased to 95% during 12 hours, held at 95% for 6 hours, linearly decreased to 2% in 12 hours and held at 2% for another 6 hours. As a result phase 4 transformed into the dihydrate after about 15 min at 95%, which in turn changed to phase 2 after about 20 min at 2% r.h.

Polymorph 4 may also be characterized by its DVS (dynamic vapor sorption) water vapor sorption and desorption isotherms. The sorption/desorption behavior of polymorph 4 is similar to the one depicted in FIG. 7 for polymorph 3.

Also storage of phase 4 at 20° C. and 75% relative humidity caused complete conversion to the dihydrate within 3 weeks. The rate of conversion apparently correlates with the relative humidity.

Maturation experiments with suspensions starting from phase mixtures in dry organic solvents indicate that in the temperature range from 0 to 40° C. phase 4 is only a metastable one.

Solvates

Moreover, the present invention relates to a 1,4-dioxane solvate, a methyl acetate solvate, and an acetonitrile solvate of 6-(Piperidin-4-yloxy)-2H-isoquinolin-1-one hydrochloride.

The 1,4-dioxane solvate according to the invention shows characteristic reflections in an X-ray powder diffractogram using CuK$\alpha_1$ radiation at 15.1 (strong) and 22.5 (strong) degrees 2theta±0.2 degrees 2theta.

In another aspect the 1,4-dioxane solvate has the property of having at least characteristic reflections in an X-ray powder diffractogram using CuK$\alpha_1$ radiation at
15.1 (strong), 19.7 (medium), 20.3 (medium), 21.6 (medium), 22.5 (strong),
23.8 (medium, 24.9 (medium), and 30.2 (medium) degrees 2theta±0.2 degrees 2theta.

Figure 9:
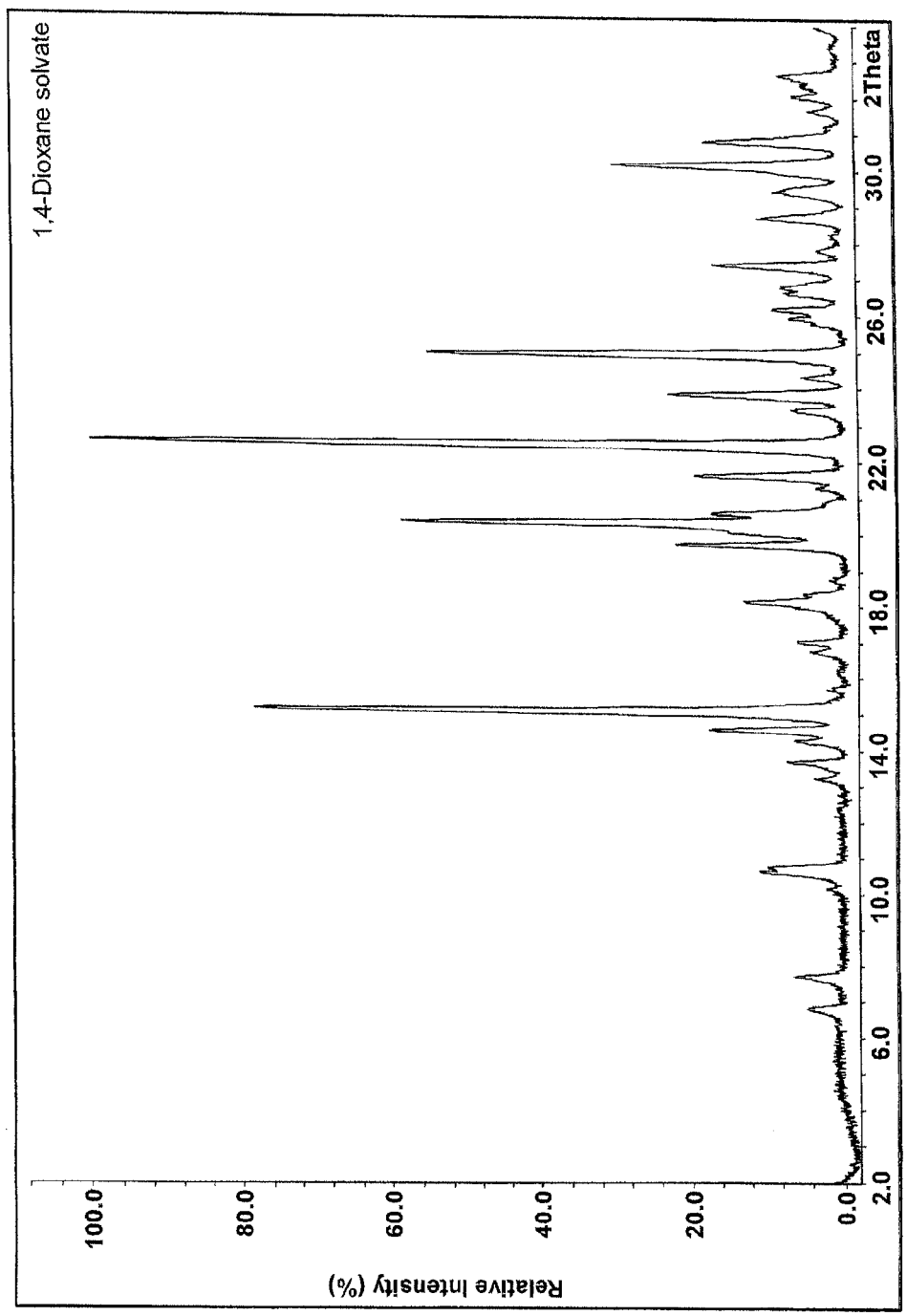
FIG. 9—X-ray powder diffraction pattern of the 1,4-dioxane solvate of compound (I), measured in transmission mode with CuK$\alpha_1$ radiation at room temperature (x-axis: diffraction angle 2theta (2θ) [°]; y-axis: relative intensity [% of the strongest reflection]).

In another embodiment, the 1,4-dioxane solvate may also be characterized by its X-ray powder diffraction pattern such as the one shown in FIG. 9. This has been obtained using CuK$\alpha_1$ radiation in transmission mode, wherein the intensities of the reflections depicted in the Figure as well as those of the reflections specified above are not a prerequisite, but may vary.

According to temperature-resolved X-ray powder diffraction, DSC and TGA, the 1,4-dioxane solvate showed a weight loss of 16.6% in the thermogravimetric analysis mainly in a temperature range from 80 to 120° C., compared with expected 16.6% for a hemi-solvate and 23.9% for one molar equivalent of dioxane. In this temperature range, transformation to phase 3 was observed as determined by XRPD. The solvate is thus relatively stable.

Thus, a further aspect of the present invention relates to the use of the 1,4-dioxane solvate for the production of polymorph 3 by drying of the 1,4-dioxane solvate at high temperature, e.g. in a temperature range from about 80 to 120° C.

In another aspect the dihydrate may be prepared by drying of the 1,4-dioxane solvate and exposure of the solvent free product to a humid atmosphere at about 0 to 40° C. to obtain the dihydrate.

The molar ratio of 1,4-dioxane and compound (I) in the 1,4-dioxane solvate can vary. In one embodiment of the invention the 1,4-dioxane content ranges from about 1.1 to about 0.1, in another embodiment from about 1.1 to about 0.3, in another embodiment from about 1 to about 0.3, in another embodiment from about 0.7 to about 0.3, in another embodiment about 0.5 molar equivalents of 1,4-dioxane which latter 1,4-dioxane content corresponds to the weight loss of samples of the dioxane solvate as determined by TGA. A particular object is thus a 6-(Piperidin-4-yloxy)-2H-isoquinolin-1-one hydrochloride×0.5 1,4-dioxane solvate.

The acetonitrile solvate is another object of the present invention. This solvate shows at least characteristic reflections in an X-ray powder diffractogram using CuK$\alpha_1$ radiation at 6.8 (medium), 11.3 (medium) and 27.7 (strong) degrees 2theta±0.2 degrees 2theta.

In another aspect the acetonitrile solvate has the property of having at least characteristic reflections in an X-ray powder diffractogram using CuK$\alpha_1$ radiation at
6.8 (medium), 11.3 (medium), 15.3 (strong), 20.9 (medium), 23.9 (strong),
24.0 (medium), 27.4 (medium), and
27.7 (strong) degrees 2theta±0.2 degrees 2theta.

Figure 10:
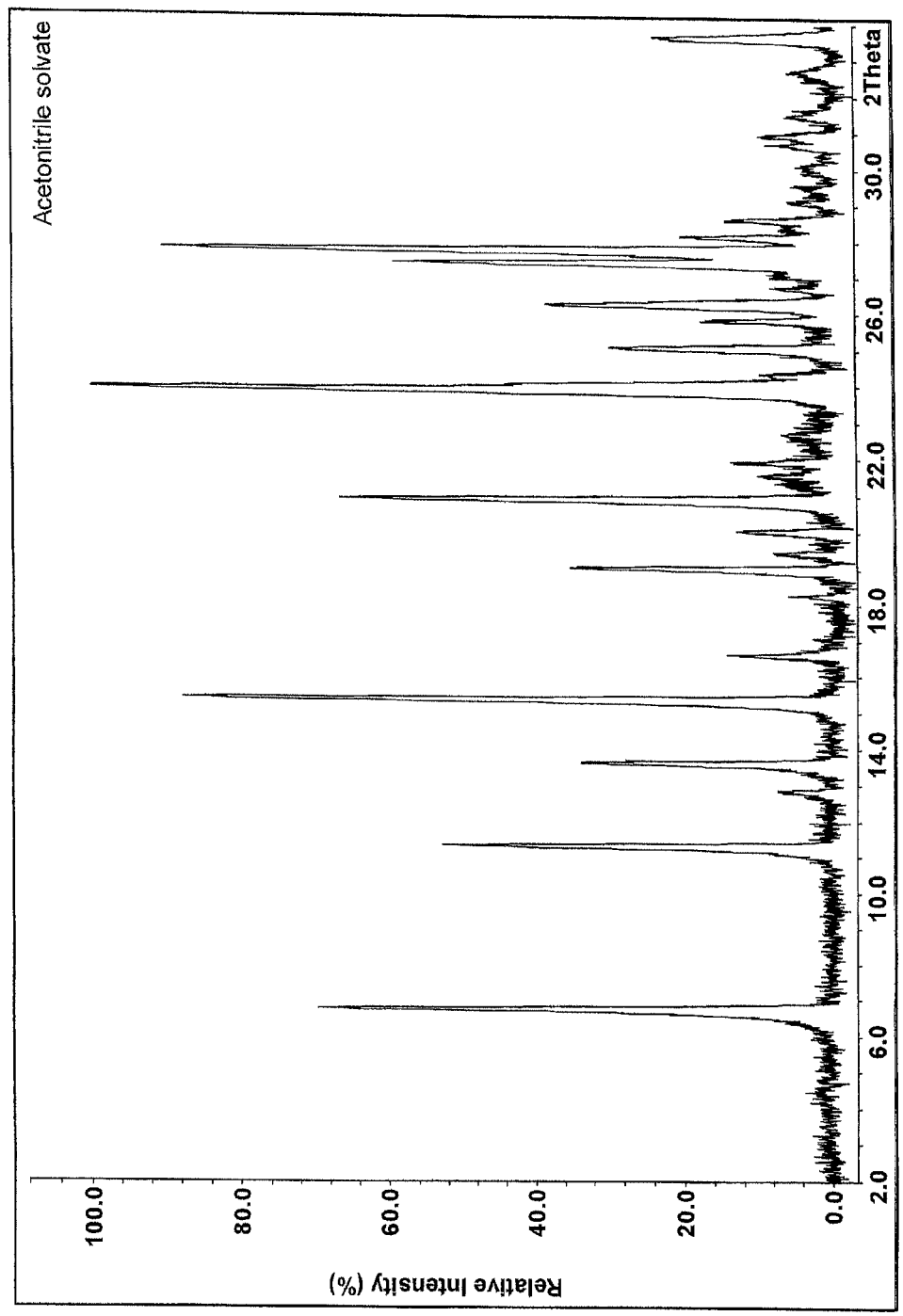
FIG. 10—X-ray powder diffraction pattern of the acetonitrile solvate of compound (I), measured in transmission mode with CuK$\alpha_1$ radiation at room temperature (x-axis: diffraction angle 2theta (2θ) [°]; y-axis: relative intensity [% of the strongest reflection]).

In another embodiment, the acetonitrile solvate may also be characterized by its X-ray powder diffraction pattern substantially as shown in FIG. 10, which has been obtained in suspension using CuK$\alpha_1$ radiation in transmission mode, wherein the intensities of the reflections depicted in the Figure as well as those of the reflections specified above are not a prerequisite, but may vary.

The acetonitrile solvate can be used in the purification of compound (I) by recrystallizing it in the form of this solvate starting from compound (I).

Thus, a further aspect of the present invention relates to the use of the acetonitrile solvate of compound (I) for purifying compound (I).

The methyl acetate solvate according to the invention shows at least characteristic reflections in an X-ray powder diffractogram measured in suspension (capillary) using CuK$\alpha_1$ radiation in transmission mode at 15.0 (strong) and 23.7 (strong) degrees 2theta±0.2 degrees 2theta.

In another aspect the methyl acetate solvate has the property of having at least characteristic reflections in an X-ray powder diffractogram using CuK$\alpha_1$ radiation at
6.9 (medium), 15.0 (strong), 20.8 (medium), 22.8 (medium), 23.7 (strong),
24.0 (medium), 25.1 (medium), and 28.0 (medium) degrees 2theta±0.2 degrees 2theta.

Figure 11:
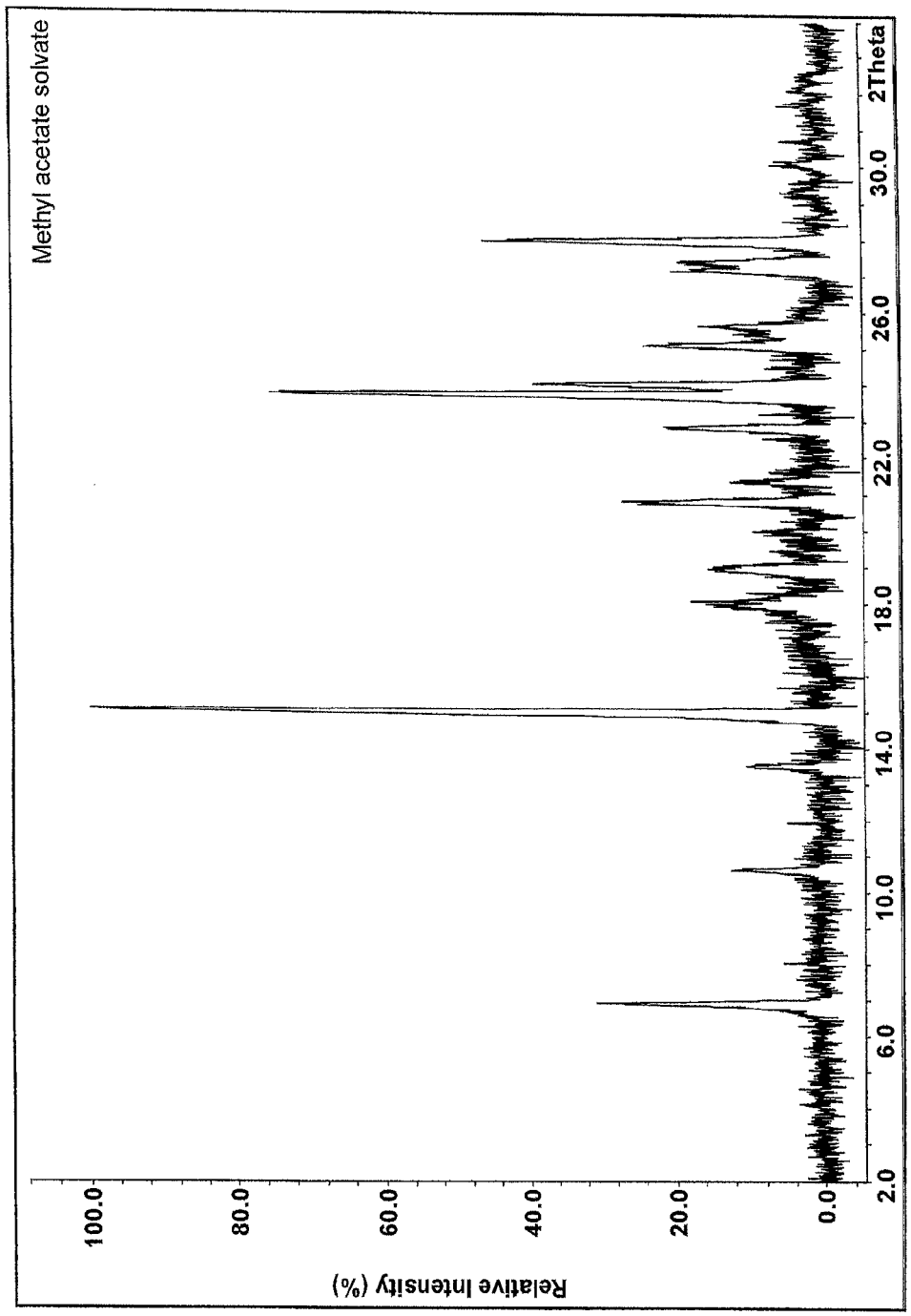
FIG. 11—X-ray powder diffraction pattern of the methyl acetate solvate of compound (I), measured in transmission mode with CuK$\alpha_1$ radiation at room temperature (x-axis: diffraction angle 2theta (2θ) [°]; y-axis: relative intensity [% of the strongest reflection]).

In another embodiment, the methyl acetate solvate may also be characterized by its X-ray powder diffraction pattern substantially as shown in FIG. 11, which has been obtained using $CuK\alpha_1$ radiation in transmission mode, wherein the intensities of the reflections depicted in the Figure as well as those of the reflections specified above are not a prerequisite, but may vary.

Outside the mother liquor, the methyl acetate solvate is only moderately stable and in the presence of humidity starts to transform to the hydrate. Thus, a further aspect of the present invention relates to the use of the methyl acetate solvate of compound (I) for the production of the hydrate, for example by subjecting it to conditions, such as an elevated temperature and/or humidity which facilitate the loss of methyl acetate and attracting water.

Another aspect of the present invention relates to the use of a polymorphic form or a mixture of polymorphic forms and of the hydrate of 6(Piperidin-4-yloxy)-2H-isoquinolin-1-one hydrochloride according to the present invention as a pharmaceutical or medicament.

In one embodiment the invention relates to the use of a polymorphic form selected from polymorphic forms 1, 2, 3, 4 and the hydrate or a mixture of these forms comprising at least one of polymorphic forms 1, 2, 3, 4, and the hydrate as a pharmaceutical or medicament.

A further aspect of the present invention relates to a solid pharmaceutical composition comprising at least one polymorphic form or solvate of 6-(Piperidin-4-yloxy)-2H-isoquinolin-1-one hydrochloride according to the present invention, especially a form selected from polymorphic forms 1, 2, 3, 4, and the hydrate and one or more pharmaceutical acceptable excipients, i.e. inactive substances such as diluents and other auxiliaries. In one embodiment of the invention the pharmaceutical composition comprises one of polymorphic forms 1, 2, 3, or 4, especially polymorph 2, and secondly the hydrate in any ratio. In another embodiment the pharmaceutical composition comprises the hydrate.

The solid pharmaceutical compositions, which can be employed when using compound (I) as a medicament in human medicine and veterinary medicine, normally contain a polymorph or polymorphs of compound (I) or the hydrate in a percentage from about 0.01% to about 90% by weight, in particular from about 0.1% to about 20% by weight, for example from about 0.1% to about 10% by weight, and with an amount from about 0.2 mg to about 100 mg, in particular from about 1 mg to about 20 mg, per unit dose, All values mentioned are calculated based on the free base 6-(Piperidin-4-yloxy)-2H-isoquinolin-1-one having a molecular weight of 244.12.

But depending on the kind of the pharmaceutical composition and other particulars of the specific case, the percentage and amount may deviate from the indicated ones.

In general, suitable excipients are known to the person skilled in the art. A diluent, or carrier substance, is any compound which is pharmaceutical acceptable and suitable to increase the bulk volume of the solid pharmaceutical composition, so that the final product has the proper form and volume for administration and dosage by the patient or physician. Examples of diluents are vegetable fats and oils, lactose, sucrose, glucose, mannitol, sorbitol, calcium carbonate, calcium phosphate, kaolin, microcrystalline cellulose, starch etc. and combinations thereof. Examples of other auxiliaries, which may be present in a pharmaceutical composition for attaining the desired property profile and/or supporting its manufacture, are antiadherents, binders (e.g. acaia gum, gelatin, cellulose, cellulose derivatives, polyvinylpyrrolidone, sodium alginate, starch, sucrose, polyethylene glycol, etc.), buffer salts, coatings (e.g. cellulose, synthetic polymers, shellac, polysacharrides etc.), disintegrants (e.g. starch, cellulose, crosslinked polyvinylpyrrolidone, sodium starch glycolate, sodium carboxymethyl cellulose, methyl cellulose, gums such as agar, guar, etc.), flavors and colors, glidants, lubricants (e.g. talc, silica, magnesium stearate etc.), preservatives (e.g. antioxidants like vitamin A, vitamin E, vitamin C, retinyl palmitate and selenium, methionine, cysteine, citric acid, sodium citrate, methylparaben, propylparaben etc.), sorbents, sweeteners, wetting agents and others including e.g. gelatin, casein, lecithin, gum acacia, cholesterol, tragacanth, stearic acid, benzalkonium chloride, calcium stearate, glycerol monostearate, cetostearyl alcohol, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, cellulose derivatives, magnesium aluminum silicate, triethanolamine, polyvinyl alcohol, polyvinylpyrrolidone etc., as well as any combination thereof.

The pharmaceutical compositions according to the invention may have any form suitable for dosage and administration in the desired use of compound (I) and, e.g., be a suspension, tablet, pill, hard or soft capsule, lozenge, and the like. The pharmaceutical compositions can be administered, for example, orally, bucally, rectally, parenterally, subcutaneously, nasally, topically, by inhalation or by ophthalmic or transdermal routes, especially orally, the preferred administration depending on the particular case. The dosage, which is employed when treating a subject, preferably a mammal, more preferably a human, with compound (I) in the form of one or more polymorphs or the hydrate according to the invention and which is effective for obtaining the desired therapeutic or prophylactic result, varies and is determined by the physician in view of the particulars of the specific case. As is known in the art, the dosage depends on a variety of factors such as, for example, the severity of the condition being treated, general health, the route of administration, body weight, gender, diet, time and route of administration, the desired duration of treatment, rates of absorption and excretion, combination with other drugs, and others. The total daily dose of a crystalline phase or a mixture of crystalline phases (anhydrous and/or hydrated) of compound (I) according to the invention may be administered to a patient in a single dose or divided doses.

Another aspect of the present invention relates to the use of a polymorphic form or a mixture of polymorphic forms and of the hydrate of 6-(Piperidin-4-yloxy)-2H-isoquinolin-1-one hydrochloride according to the present invention as a pharmaceutical or medicament in combination with one or more further pharmacologically active ingredients which have, for example, favourable effects on metabolic disturbances or disorders frequently associated therewith. Examples of such medicaments are 1. medicaments which lower blood glucose, antidiabetics,
 2. active ingredients for the treatment and/or prevention of complications caused by diabetes or associated with diabetes,
 3. active ingredients for the treatment of dyslipidemias,
 4. antiatherosclerotic medicaments,
 5. antiobesity agents,
 6. antiinflammatory active ingredients,
 7. antithrombotic active ingredients,
 8. active ingredients for the treatment of high blood pressure,
 9. active ingredients for the treatment of heart failure.

They can be combined with the inventive compounds of the formula (I), in particular for a synergistic improvement in the effect. Administration of the active ingredient combination can take place either by separate administration of the active ingredients to the patient or in the form of combination products in which a plurality of active ingredients are present in one pharmaceutical preparation.

Suitable further active ingredients for the combination products are especially: All antidiabetic agents which are mentioned in the Rote Liste 2011, Chapter 12; all anti hypertension agents which are mentioned in the Rote Liste 2011, Chapter 17; all slimming agents/appetite suppressants which are mentioned in the Rote Liste 2011, Chapter 19; all beta receptor blocker, calcium channel blocker and inhibitors of rennin-angiotensin-system which are mentioned in the Rote Liste 2011, Chapter 27, for example Amlodipin; all slimming agents/appetite suppressants which are mentioned in the Rote Liste 2011, Chapter 1; all lipid reducers which are mentioned in the Rote Liste 2011, Chapter 58. In one embodiment they can be combined with ACE (Angiotensin Converting Enzyme) inhibitors such as Benazepril, Captopril, Cilazapril, Enalapril, Fosinopril, Imidapril, Lisinopril, Moexipril, Perindopril, Quinapril, Ramipril, Spirapril, Trandolapril or Zofenopril.

In one embodiment they can be combined with calcium channel blockers such as Verapamil, Gallopamil, Fendilin, Diltiazem, Nitrendipin, Felodipin, Amlodipin, Nifedipin, Lercanidipin, Nimodipin, Nicardipin, Lacidipin, Isradipin, Nisoldipin, Nilvadipin or Manidipin.

They can be combined with the inventive compound of the formula I especially for synergistic improvement of action. The active ingredient combination can be administered either by separate addition of the active ingredients to the patient or in the form of combination preparations in which a plurality of active ingredients are present in a pharmaceutical formulation. Most of the active ingredients mentioned below are disclosed in USP Dictionary of USAN and International Drug Names, US Pharmacopeia, Rockville 2006.

In one embodiment of the present invention, an anhydrous phase or a mixture of anhydrous phases of compound (I) and/or the hydrate according to the invention, or a pharmaceutical composition comprising them, is used in the treatment, including therapy and/or prophylaxis/prevention, of diseases associated with Rho-kinase and/or Rho-kinase mediated phosphorylation of myosin light chain phosphatase, in particular for the treatment and/or prevention of hypertension, pulmonary hypertension, ocular hypertension, retinopathy, glaucoma, peripheral circulatory disorder, peripheral occlusive arterial disease (PAOD), coronary heart disease, angina pectoris, heart hypertrophy, heart failure, ischemic diseases, end organ damage incl. ischemic organ failure, fibroid lung, fibroid liver, liver failure, nephropathy (including hypertension-induced, non-hypertension-induced, and diabetic nephropathies), renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain; neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, osteopathy such as osteoporosis, infection of digestive tracts with bacteria, sepsis, cancer development and progression, e.g. cancers of the breast, colon, prostate, ovaries, brain and lung and their metastases.

Accordingly, a further aspect of the present invention relates to the use of a polymorphic form or a mixture of polymorphic forms and/or the hydrate of 6-(Piperidin-4-yloxy)-2H-isoquinolin-1-one hydrochloride according to the invention for the manufacture of a medicament, especially a medicament for the treatment, including therapy and/or prophylaxis/prevention, of hypertension, pulmonary hypertension, ocular hypertension, retinopathy, glaucoma, peripheral circulatory disorder, peripheral occlusive arterial disease (PAOD), coronary heart disease, angina pectoris, heart hypertrophy, heart failure, ischemic diseases, end organ damage in ischemic organ failure, fibroid lung, fibroid liver, liver failure; nephropathy, including hypertension-induced, non-hypertension-induced and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain; neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

According to one embodiment of the invention, the pharmaceutical composition according to the invention contains polymorph 1 of compound (I). According to another embodiment, it contains polymorph 1 of compound (I) in combination with polymorph 2 of compound (I) and/or polymorph 3 of compound (I) and/or polymorph 4 of compound (I), for example polymorph 1 of compound (I) in combination with polymorph 3 of compound (I) or polymorph 1 of compound (I) in combination with polymorph 4 of compound (I). According to another embodiment of the invention, the pharmaceutical composition according to the invention contains polymorph 3 of compound (I). According to another embodiment, it contains polymorph 3 of compound (I) in combination with polymorph 1 of compound (I) and/or polymorph 2 of compound (I) and/or polymorph 4 of compound (I), for example polymorph 3 of compound (I) in combination with polymorph 4.

According to another embodiment of the invention, the pharmaceutical composition according to the invention contains polymorph 4 of compound (I). According to another embodiment, it contains polymorph 4 of compound (I) in combination with polymorph 1 of compound (I) and/or polymorph 2 of compound (I) and/or polymorph 3 of compound (I), for example polymorph 4 of compound (I) in combination with polymorph 2. According to another embodiment of the invention, the pharmaceutical composition contains the hydrate of compound (I). According to another embodiment, the pharmaceutical composition contains the hydrate of compound (I) in combination with polymorph 1 of compound (I) and/or polymorph 2 of compound (I) and/or polymorph 4 of compound (I), for example the hydrate of compound (I) in combination with polymorph 2. In an embodiment of the present invention the hydrate is used alone, i.e. it is used substantially free of the other polymorphs, in the pharmaceutical composition. Substantially free means that it contains less than 10%, preferably less than 5%, more preferably less than 1% of one or more of the other polymorphs, especially of polymorph 2.

Another aspect of the present invention relates to processes for the preparation of the polymorphic forms and solvates according to the invention. In a further aspect, the present invention relates to a process for the purification of 6-(Piperidin-4-yloxy)-2H-isoquinolin-1-one hydrochloride comprising a crystallization step, wherein polymorph 1, polymorph 2, polymorph 3, polymorph 4, or the hydrate of 6-(Piperidin-4-yloxy)-2H-isoquinolin-1-one hydrochloride described above is obtained. Said process comprises preferably the preparation of polymorph 1, polymorph 2, polymorph 3, polymorph 4, or a dihydrate as outlined below. In another embodiment of a process for purification of 6-(Piperidin-4-yloxy)-2H-isoquinolin-1-one hydrochloride a methyl acetate solvate, 1,4 dioxane solvate or acetonitrile solvate thereof may be prepared and used.

In general, the polymorphic forms and solvates of the invention can be obtained by crystallizing or recrystallizing compound (I), starting from a solution of compound (I) or from a suspension of compound (I) or from solid compound (I). A solution of compound (I), or a suspension of compound (I), may have been obtained at the end of the chemical synthesis of compound (I), or it may have been obtained by dissolving or suspending previously synthesized crude compound (I). The term "crude compound (I)" comprises any form of compound (I), e.g. the material directly obtained from chemical synthesis, a distinct polymorphic form or solvate or a mixture of polymorphic forms and/or solvates, which may not have been characterized with respect to its crystal properties, and which is to be transformed to a distinct polymorphic form or solvate or to another distinct polymorphic form or solvate.

More specifically, the polymorphic forms 1, 3 and 4 and solvates of the invention can be obtained by (a) providing a solution or suspension of compound (I), for example by dissolving or suspending crude compound (I) in a suitable solvent such as an alcohol, e.g. methanol, ethanol, isopropanol; a ketone, e.g. acetone or methyl ethyl ketone; an ether, e.g. tetrahydrofuran or dioxane; or other solvents such as acetonitril or methyl acetate, wherein a solution of compound (I) generally is a clear solution and may optionally have been filtered, (b) maintaining, heating, cooling and/or concentrating the solution or suspension and/or adding one or more further solvents, with or without agitation such as stirring, to form crystals of a desired distinct polymorph or solvate or to allow the formation of a desired distinct polymorph or solvate, and (c) isolating the distinct polymorph or solvate.

The processes for preparing polymorphic forms and solvates of compound (I) can be performed with conventional equipment and according to standard procedures. For example, concentrating of a solution or suspension in step (b) may be done by distilling off solvent partially or totally at atmospheric pressure or at reduced pressure. Isolating of a polymorph or solvate in step (c) may be done by any conventional technique such as filtration or vacuum filtration or centrifugation. Isolating may also comprise drying, e.g. by applying elevated temperatures and/or reduced pressure, for example at moderately reduced pressure at about room temperature, i.e. a temperature of about 18° C. to about 25° C., for example about 20° C., or at about 40° C.

In a preferred embodiment, the solution or suspension may be seeded in step (a) or step (b) to promote crystallization or polymorph transformation. Seeding is preferably done with a small amount of the desired polymorph or solvate, for example polymorph 1, polymorph 3 or polymorph 4.

A further aspect of the present invention relates to a process for the preparation of 6-(Piperidin-4-yloxy)-2H-isoquinolin-1-one hydrochloride dihydrate, the process comprising the steps of (a) dissolving 6-(Piperidin-4-yloxy)-2H-isoquinolin-1-one hydrochloride in a suitable solvent containing water or in water alone at a temperature suitable to obtain a solution, (b) concentrating the solution by evaporating the solvent partially sufficient to allow formation of dihydrate crystals or cooling down the solution and maintaining it for a time period sufficient to allow formation of dihydrate crystals and (c) isolating the dihydrate.

A suitable solvent or solvent mixture for dissolving and crystallizing 6-(Piperidin-4-yloxy)-2H-isoquinolin-1-one may be selected from acetone/water, methyl ethyl ketone/water, methanol/water, ethanol/water, isopropanol/water, tetrahydrofuran/water, acetonitril/water or water.

The temperature suitable to obtain a solution is from about 55° C. to about 70° C., preferably at about 65° C.

The period sufficient to allow formation of a precipitate of dihydrate crystals by concentrating is for example from about 1 hour to 10 days, such as about 2 days. Cooling down of the solution may for example be performed by letting it stand at room temperature and/or by active cooling within about 1 minute to about 30 minutes, and may vary depending on the sample size. The temperature obtained by cooling is about 0° C.

The water content in the solvent mixtures mentioned above may vary depending on the solvent used but can vary in a broad range for the organic solvent and water. It can e.g. be in the range of about 4:1-1:4 (v/v) for solvent mixtures such as ethanol/water, 2-propanol/water, or acetone/water, but it can be even more water and also pure water may be used. In one embodiment a solvent/water mixture of 4:1 is used. In another embodiment, acetone/water mixture is used. In one embodiment a ratio of 3:1 (v/v), in other embodiment a range of 3:2 (v/v) acetone/water is used.

According to a preferred embodiment, the solution may be seeded with dihydrate crystals, preferably during step (b).

Drying of the dihydrate obtained can be done e.g. with a stream of nitrogen having a defined humidity (more than about 30% water) in order to avoid an overdrying of the dihydrate and a loss of water from the crystal.

A further aspect of the present invention relates to a process for the preparation of polymorph 2 of 6-(Piperidin-4-yloxy)-2H-isoquinolin-1-one hydrochloride, the process comprising the steps of (a) exposing 6-(Piperidin-4-yloxy)-2H-isoquinolin-1-one hydrochloride dihydrate at a temperature of about 20 to about 40° C. to rather low humidity, preferably a gas, such as nitrogen or air, with less than 2% relative humidity;

(b) maintaining the 6-(Piperidin-4-yloxy)-2H-isoquinolin-1-one hydrochloride dihydrate at about room temperature for a time period sufficient to allow formation of polymorph 2 of compound (I), for example for about 1 day to about 50 days, such as for about 28 days; and (c) isolating polymorph 2.

The time period of exposure to air may vary depending on the size of the sample and may also be less than one day for small samples.

One aspect of the present invention relates to a process for the preparation of polymorph 1 of 6-(Piperidin-4-yloxy)-2H-isoquinolin-1-one hydrochloride, the process comprising the steps of a) dissolving 6-(Piperidin-4-yloxy)-2H-isoquinolin-1-one hydrochloride or the dihydrate thereof in a solvent mixture of methanol and isopropanol, preferably in a ratio of about 2 to 1, to obtain a solution, preferably by heating at a temperature of about 55° C. to about 65° C.;

(b) cooling, for example to a temperature of about 0° C., for a time period sufficient to allow formation of polymorph 1 crystals, for example for about 30 minutes to about 4 hours; and (c) isolating polymorph 1.

A further aspect of the present invention relates to a process for the preparation of polymorph 3 of 6-(Piperidin-4-yloxy)-2H-isoquinolin-1-one hydrochloride, the process comprising the steps of (a) dissolving 6-(Piperidin-4-yloxy)-2H-isoquinolin-1-one hydrochloride or the dihydrate thereof in a suitable solvent such as methanol to obtain a solution, for example at about room temperature or at a temperature of about 55° C. to about 65° C.;

(b) cooling, for example to a temperature of about 0° C., for a time period sufficient to allow formation of polymorph 3 crystals, for example for about 30 minutes to about 4 hours; and (c) isolating polymorph 3;

or (a') suspending 6-(Piperidin-4-yloxy)-2H-isoquinolin-1-one hydrochloride dihydrate at about room temperature in a solvent selected from the group consisting of methanol, ethanol, 1-propanol, 2-propanol and acetone to obtain a suspension;

(b') maintaining the suspension at a temperature of about 0° C. to about 45° C., preferably about 15° C. to about 25° C., more preferably at about 20° C., for a time period sufficient to allow formation of polymorph 3 crystals, for example for about 1 day to about 50 days, such as for about 35 days; and (c') isolating polymorph 3.

Depending on the crystallization conditions, in this process polymorph 3 may be obtained together with another polymorph, for example polymorph 1 or 4. According to a preferred embodiment, the solution may be seeded with polymorph 3 crystals, preferably during step (b).

A further aspect of the present invention relates to a process for the preparation of polymorph 4 of 6-(Piperidin-4-yloxy)-2H-isoquinolin-1-one hydrochloride, the process comprising the steps of (a) suspending 6-(Piperidin-4-yloxy)-2H-isoquinolin-1-one hydrochloride dihydrate at about room temperature in 2-butanol to obtain a suspension;

(b) maintaining the suspension at a temperature of about 0° C. to about 45° C., preferably about 15° C. to about 25° C., more preferably at about 20° C., for a time period sufficient to allow formation of polymorph 4 crystals, for example for about 1 day to about 50 days, such as for about 35 days;

(c) isolating polymorph 4.

According to a preferred embodiment, the solution may be seeded with polymorph 4 crystals, preferably during step (b).

A further aspect of the present invention relates to a process for the preparation of methyl acetate solvate of 6-(Piperidin-4-yloxy)-2H-isoquinolin-1-one hydrochloride, the process comprising the steps of (a) suspending 6-(Piperidin-4-yloxy)-2H-isoquinolin-1-one hydrochloride dihydrate at about room temperature in methyl acetate to obtain a suspension;

(b) maintaining the suspension at about room temperature for a time period sufficient to form methyl acetate solvate, for example for about 1 day to about 50 days, such as for about 35 days;

(c) isolating the methyl acetate solvate.

Depending on the isolation conditions the solvate may partially transform into other polymorphs such as the dihydrate, forms 1 or 3.

A further aspect of the present invention relates to a process for the preparation of 1,4-dioxane solvate of 6-(Piperidin-4-yloxy)-2H-isoquinolin-1-one hydrochloride, the process comprising the steps of (a) suspending 6-(Piperidin-4-yloxy)-2H-isoquinolin-1-one hydrochloride dihydrate at about room temperature in 1,4-dioxane to obtain a suspension;

(b) maintaining the suspension at about room temperature for a time period sufficient to allow formation of 1,4-dioxane solvate, for example for about 1 day to about 50 days, such as for about 28 days;

(c) isolating the precipitate of 1,4-dioxane solvate.

Depending on the isolation conditions the dioxane solvate and additionally the dihydrate may be obtained.

In a further aspect of the present invention relates to a process for the preparation of acetonitrile solvate of 6-(Piperidin-4-yloxy)-2H-isoquinolin-1-one hydrochloride, the process comprising the steps of (a) suspending 6-(Piperidin-4-yloxy)-2H-isoquinolin-1-one hydrochloride dihydrate at about room temperature in acetonitrile to obtain a suspension;

(b) maintaining the suspension at about room temperature for a time period sufficient to allow formation of acetonitrile solvate, for example for about 1 day to about 50 days, such as for about 35 days;

(c) isolating the precipitate of acetonitrile solvate.

Depending on the isolation conditions the acetonitrile solvate but also the dihydrate as well as additionally forms 1 and 3 may be obtained.

EXAMPLES

The following examples illustrate the formation of the polymorphs and solvates of the present invention by way of example. Compound (I) as starting material for making the polymorphs and solvates can be obtained as described in WO 2007/012421. Where the dihydrate is used or obtained, this is specified. 6-(Piperidin-4-yloxy)-2H-isoquinolin-1-one hydrochloride is abbreviated as "compound (I)".

If not mentioned otherwise drying was carried out in all formation and maturation experiments mentioned below over night at reduced pressure (about <50 mbar) at 40° C. The polymorphs, hydrate and solvates were identified and characterized by their XRPD pattern.

1) Formation of Dihydrate

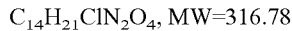

$C_{14}H_{21}ClN_2O_4$, MW=316.78 a) 10 g crude 6-(Piperidin-4-yloxy)-2H-isoquinolin-1-one hydrochloride were dissolved in 25 mL water at 70 C. The solution was cooled to 55° C. and 75 mL acetone were added. The mixture was cooled to room temperature within 3 hours and left standing for two days for crystallization. After cooling (4° C.) for 6 hours the product was isolated via filtration, washed with acetone/water (3:1) and dried in vacuum. 7.9 g (purity 97.1%) of 6-(Piperidin-4-yloxy)-2H-isoquinolin-1-one hydrochloride dihydrate were obtained. Water content (Karl Fischer): 10.52% b) 8.5 g of crude 6-(Piperidin-4-yloxy)-2H-isoquinolin-1-one hydrochloride were dissolved in 21.5 mL water at 65° C. The temperature was lowered to 50° C. in 1 h and 32.3 mL acetone were added in 30 min. The temperature was lowered to 40° C. and the mixture was stirred for 3 h. The reaction mixture was chilled to ambient temperature. The crystalline material was collected, washed with water/acetone (1/3) and dried to yield 4.54 g (purity>99.9%) of 6-(Piperidin-4-yloxy)-2H-isoquinolin-1-one hydrochloride dihydrate.

Water content (Karl Fischer) 10.6%

$^1$H NMR (500 MHz, d$_6$-DMSO) δ 1.85-1.95 (m, 2H), 2.13-2.22 (m, 2H), 3.04-3.14 (m, 2H), 3.20-3.29 (m, 2H), 4.79-4.86 (m, 1H), 6.44 (d, J=7.1 Hz, 1H), 7.10 (dd, J=8.9, 2.5 Hz, 1H), 7.14 (dd, J=7.2, 6.7 Hz, 1H), 7.22 (d, J=2.5 Hz, 1H), 8.09 (d, J=8.6 Hz, 1H), 8.97-9.13 (bs, 2H) 11.09 (bd, J=5 Hz, 1H).

c) 0.205 g compound (I) (dihydrate) were dissolved in 20 mL ethanol and 3 mL water at about 65° C. The solvent was allowed to evaporate from the stirred solution at the same temperature over night.

d) 0.200 g of compound (I) (dihydrate) were dissolved in 20 mL ethanol and 4 mL water at 65° C. The solution was rapidly cooled to 0° C. After 45 minutes the product was isolated by vacuum filtration and dried.

In the same manner the dihydrate was obtained if ethanol was replaced by tetrahydrofuran or methyl ethyl ketone in examples c) and d).

e) 0.204 g of compound (I) (dihydrate) were dissolved in 3 mL water at 65° C. The solution was rapidly cooled to 0° C. After 30 minutes the product was isolated by vacuum filtration and dried.

2) Formation of Polymorph 1

$C_{14}H_{17}N_2O_2Cl$, MW=280.76

1.2 g of 6-(Piperidin-4-yloxy)-2H-isoquinolin-1-one hydrochloride were suspended in isopropanol and stirred for 6 h. The solid material (1.14 g) was isolated by filtration. 60.7 mg thereof were suspended in a mixture of 0.352 mL isopropanol and 0.647 mL methanol. The mixture was heated until a clear solution was obtained. Upon cooling the crystalline product was obtained which was isolated by filtration.

3) Formation of Polymorph 2

$C_{14}H_{17}N_2O_2Cl$, MW=280.76

About 3 mg of compound (I) (dihydrate) were at 25° C. exposed to a dry nitrogen atmosphere (stream of nitrogen) for at least 6 hours. After this treatment, the X-ray diffraction pattern of the sample corresponds to phase 2.

4) Formation of Polymorph 3

$C_{14}H_{17}N_2O_2Cl$, MW=280.76 a) 0.201 g of compound (I) (dihydrate) were dissolved in 20 mL acetonitril and 3 mL water at 65° C. The solvent was allowed to evaporate from the stirred solution at the same temperature over night. Polymorph 3 and traces of the dihydrate were obtained.

b) 0.208 g of compound (I) (dihydrate) were dissolved in 10 mL methanol at 65° C. The stirred solution was rapidly cooled to 0° C. After 30 minutes the product was isolated by vacuum filtration and dried.

c) 0.203 g of compound (I) (dihydrate) were suspended in 1.2 mL methanol at 20° C. and stirred for 35 days. The product was isolated by vacuum filtration and dried.

The same product (polymorph 3) was obtained, if the dihydrate of compound (I) was suspended in ethanol, 1-propanol or 2-propanol.

5) Formation of Polymorph 4

$C_{14}H_{17}N_2O_2Cl$, MW=280.76 a) 0.202 g of compound (I) (dihydrate) were suspended in 2.0 mL 2-butanol at 20° C. and stirred for 35 days. The product was isolated by vacuum filtration and dried.

6) Formation of Methyl Acetate Solvate a) 0.208 g of compound (I) (dihydrate) were suspended in 2.5 mL of methyl acetate. The solution was stirred in a closed vessel at room temperature for 35 days. The solid present in the suspension was the methyl acetate solvate as determined by XRPD in suspension.

After vacuum filtration and drying the dihydrate containing forms 1 and 3 was obtained.

7) Formation of 1,4 Dioxane Solvate a) 0.204 g of compound (I) (dihydrate) were dissolved in 2.5 mL of 1,4-dioxane at 20° C. for 35 days with continuous stirring. The solid present in the suspension was the methyl acetate solvate as determined by XRPD in suspension.

After vacuum filtration and drying the solvate containing dihydrate were obtained 8) Formation of Acetonitrile Solvate a) 0.206 g of compound (I) (dihydrate) were suspended in 2.5 mL of acetonitrile. The suspension was stirred at 20° C. for 35 days. The solid present in the suspension was the acetonitrile solvate as determined by XRPD in suspension.

The solid present in the suspension was isolated via vacuum filtration and dried overnight at reduced pressure at room temperature.

After vacuum filtration and drying the dihydrate containing forms 1 and 3 was obtained.

9) Maturation Examples

By maturation experiments (slurry conversion) at the given temperature the relative stability of the polymorphs of compound (I) and the hydrate was investigated.

The following maturation experiment was performed by stirring the suspension under the specified conditions, starting from the dihydrate. The sample was investigated by XRPD in suspension, after vacuum filtration as well as after drying over night at 40° C. in vacuum (<50 mbar). The isolated material was also investigated by DSC and TGA.

a) Maturation of 0.210 g dihydrate of compound (I) in 0.4 mL of water at 20° C. for 35 days. Similar, maturation of the dihydrate was done in water/methanol (vol/vol 1:1) and in water/ethanol (vol/vol 1:1). In all maturation experiments the solid remained as dihydrate.

The following maturation experiments were performed by stirring the suspension under the specified conditions and isolating the solid by vacuum filtration, starting from dihydrate of compound (I). The sample was investigated by XRPD in suspension, after vacuum filtration as well as after drying. The isolated material was also investigated by DSC and TGA.

(b) Maturation of 0.203 g of dihydrate of compound (I) in 1.2 mL of methanol at 20° C. for 35 days.

(c) Maturation was also done as in (b) by using ethanol, 1-propanol or 2-propanol.

In all experiments (b) and (c) polymorph 3 was obtained.

d) Maturation of 0.202 of dihydrate of compound (I) in 2.0 mL of 2-butanol at 20° C. for 35 days. Polymorph 4 was obtained after drying.

The following maturation experiments of suspensions of phase mixtures of the dihydrate of compound (I) and phases consisting of polymorphs 1, 3 and 4 were performed at 0, and 40° C. The product was isolated by vacuum filtration and analyzed after drying.

e) Maturation of a mixture of 0.3 mg phase 1, 23.9 mg phase 3, 29.9 mg phase 4 and 27.9 mg of the dihydrate in 0.7 mL 2-propanol at 0° C. for 2 weeks.

f) Maturation of a mixture of 0.3 mg phase 1, 27.2 mg phase 3, 18.1 mg phase 4 and 29.6 mg of the dihydrate in 2.0 mL 2-butanol at 0° C. for 2 weeks.

g) Similar experiments as in e) and f) were done with corresponding mixtures of phase 1, phase 3, phase 4 and the dihydrate in 2-propanol and 2-butanol at 20° C. and at 40° C., respectively In all experiments e), f) and g) polymorph 3 was obtained after filtration and drying.

The performed maturation experiments prove that among the found polymorphs phase 3 is the thermodynamically most stable anhydrous form in the investigated temperature range.

10) Formation of Amorphous Compound (I)

Figure 12:
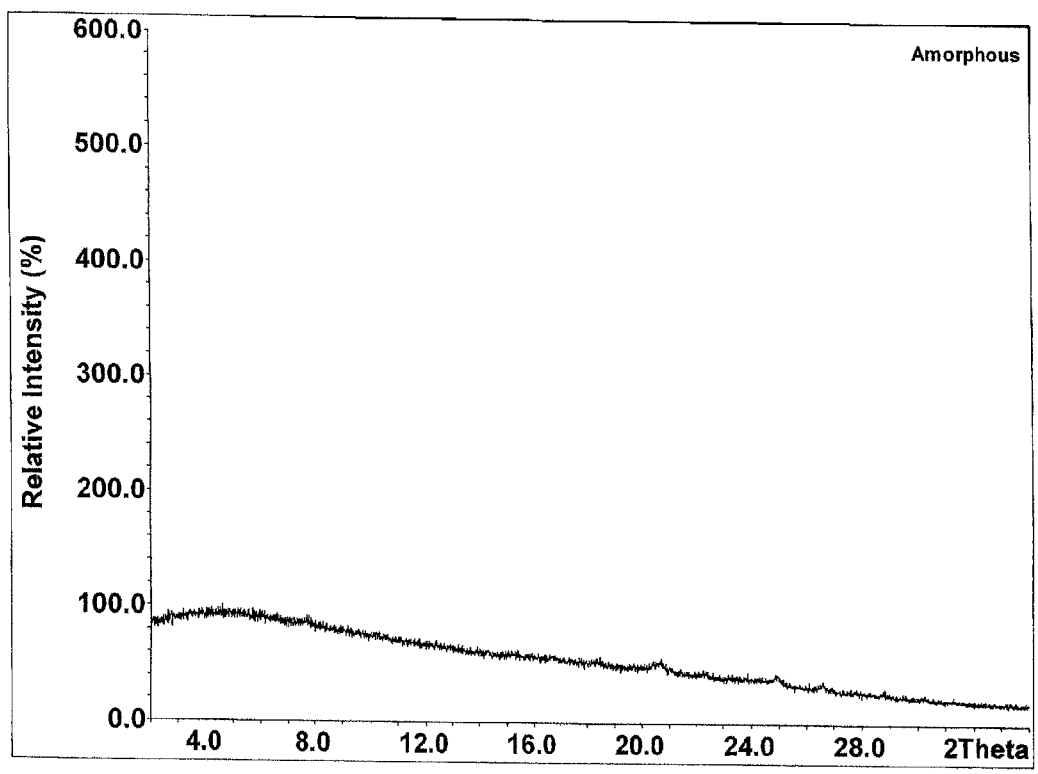
FIG. 12—X-ray powder diffraction pattern of the amorphous form of compound (I) measured in transmission mode with CuK$\alpha_1$ radiation at room temperature (x-axis: diffraction angle 2theta (2θ) [°]; y-axis: relative intensity [% of maximum intensity of amorphous halo]).

80 mg of 6-(Piperidin-4-yloxy)-2H-isoquinolin-1-one hydrochloride were dissolved in 40 mL of water and the solution was subjected to lyophilisation: The solution was frozen in liquid nitrogen and exposed to a high vacuum for about 16 hours. The obtained lyophilisate was then subjected to X-ray powder diffraction, which proved that the obtained sample is amorphous as determined by X-ray (FIG. 12).

The invention also relates to new crystalline solvates of 6-(Piperidin-4-yloxy)-2H-isoquinolin-1-one hydrochloride, in which one or more non-acidic hydrogen atom(s) were replaced by Deuterium, processes for their preparation and their use, in particular for the preparation of medicaments. The processes for their preparation can be analogue to the processes described above using the respective deuterated compounds.

Analytical Methods and Operation Conditions
X-Ray Powder Diffraction (XRPD)

All X-ray powder diffraction was performed with Stoe Stadi-P transmission diffractometers using CuK$\alpha_1$ radiation (Lambda is 1.54060 Angström). For room temperature powder diffraction, linear position sensitive detectors were used; while for temperature-resolved XRPD image plate position sensitive detectors (IP-PSDs) were used. Unless stated otherwise, X-ray powder diffraction was performed at room temperature. Dry samples were investigated in a flat preparation whereas suspensions were investigated in quartz glass capillaries. The measured data were evaluated and plotted with the Software WinXPOW V2.12.

The observed X-ray powder diffractograms of phases 1, 2, 3 and 4, the dihydrate as well as of the methyl-acetate solvate, 1,4-dioxane solvate and acetonitrile solvate of compound (I) are displayed in the Figures. The X-ray powder diffraction patterns shown in the Figures are background-substracted.

The 2θ (2theta) angles in ° (degree) are specified. The specified 2θ (2theta) angles in ° (degree) were understood with a potential variance of ±0.6 degrees 2theta.

The relative intensities of characteristic reflections are specified as follows. The relative intensity of a reflection is designated as "strong" if it is more than 75% of the intensity of the most intense reflection or it is the most intense reflection itself, and as "medium" if it is between 20% and 75% of the intensity of the most intense reflection. Below 20% the intensity is designated "weak".

Temperature-resolved X-ray powder diffractograms showed that phases 1, 2, 3, and 4 of compound (I) melted without preceding solid-solid transitions.

Thermogravimetric Analysis (TGA)

The thermogravimetric analyses were performed with a METTLER TGA851e (module TGA/SDTA851e/SF1100/042). 100 μl Al crucibles sealed with lid were used. The sample changer punches a pinhole into the lid immediately before the start of the measurement. The oven cell is purged with a nitrogen gas flow of about 50 mL/min. The measurements typically start with a hold time of about 25 min at 25° C., followed by heating of the sample with a rate of 10°/min.

Temperature and weight loss were checked by a calcium oxalate hydrate reference sample.

Differential Scanning Calorimetry (DSC)

All DSC measurements were performed with a Mettler DSC822e (module DSC822e/700/109/414935/0025). If not indicated differently, 40 μl Al crucibles with sealed lid and hole were used. All measurements were carried out in a nitrogen gas flow of 50 mL/minute. The heating rate was 10° C./minute unless indicated otherwise. Temperature and heat flow were calibrated via the melting peak of an indium reference The measured data were evaluated with the software STARe V6.1.

Dynamic Vapor Sorption (DVS)

Moisture sorption/desorption isotherms were recorded on a DVS-1 from Surface Measurement Systems. Two cycles were run at 25° C., in which the sample was first treated with dry nitrogen gas and then the relative humidity was stepwise increased from 0 to 95% and subsequently decreased again back to 0% and the weight of the sample was measured. Typical total measurement times for both cycles are about 20-30 hours.

The data were evaluated with the software DVSWin V. 2.15.

Crystal Structures

The crystal structure of the dihydrate of compound (I) was determined by X-ray single crystal structure analysis. Single crystal X-ray diffraction data were collected at room temperature on a Bruker/AXS three circle diffractometer, equipped with a SMART APEX area detector, and a molybdenum Kα rotating anode generator, operated at 50 kV/120 mA and adjusted to a fine focus of 0.5×5 mm².

The invention claimed is:

1. A crystalline hydrate of 6-(Piperidin-4-yloxy)-2H-isoquinolin-1-one hydrochloride having the formula

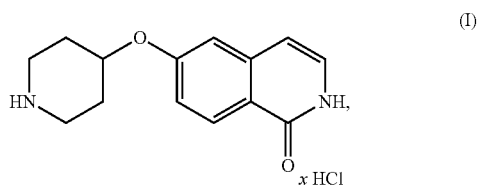 [SMILES: O=c1[nH]ccc2cc(OC3CCNCC3)ccc12]

wherein the hydrate contains 1.85 to 2.2 molecules water per molecule.

2. The hydrate according to claim 1, wherein the hydrate contains 2.0 molecules water per molecule.

3. The hydrate according to claim 1, wherein the hydrate contains 10.5-12.5% (w/w) water.

4. A crystalline hydrate of 6-(Piperidin-4-yloxy)-2H-isoquinolin-1-one hydrochloride having the formula

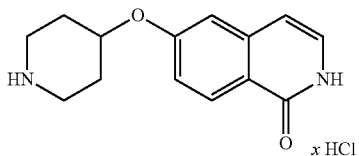

having a reflection in an X-ray powder diffractogram using CuKα₁ radiation at 7.7±0.2 degrees 2theta.

5. The hydrate according to claim 4, having reflections in an X-ray powder diffractogram using CuKα₁ radiation at 7.7, 15.2 and 16.8 degrees 2theta±0.2 degrees 2theta.

6. The hydrate according to claim 4, having reflections in an X-ray powder diffractogram using CuKα₁ radiation at 7.7, 15.2, 16.8, 22.4, 25.0, and 26.6 degrees 2theta±0.2 degrees 2theta.

7. A pharmaceutical composition comprising the hydrate of 6-(Piperidin-4-yloxy)-2H-isoquinolin-1-one hydrochloride according to claim 1.

8. A method of treating or preventing hypertension, pulmonary hypertension, ocular hypertension, retinopathy, glaucoma, peripheral circulatory disorder, peripheral occlusive arterial disease (PAOD), coronary heart disease, angina pectoris, heart hypertrophy, heart failure, ischemic diseases, end organ damage, fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, osteopathy, infection of digestive tracts with bacteria, sepsis or cancer development and progression in a patient in need thereof comprising administering to said patient a therapeutically effective amount of the pharmaceutical composition according to claim 7.

9. A method of treating or preventing nephropathy in a patient in need thereof comprising administering to said patient a therapeutically effective amount of the pharmaceutical composition according to claim 7.

10. The method according to claim 9, wherein nephropathy is diabetic nephropathy.

11. A solid pharmaceutical composition comprising the hydrate of 6-(Piperidin-4-yloxy)-2H-isoquinolin-1-one hydrochloride according to claim 1 and one or more pharmaceutical acceptable excipients.

12. A method of treating or preventing hypertension, pulmonary hypertension, ocular hypertension, retinopathy, glaucoma, peripheral circulatory disorder, peripheral occlusive arterial disease (PAOD), coronary heart disease, angina pectoris, heart hypertrophy, heart failure, ischemic diseases, end organ damage, fibroid lung, fibroid liver, liver failure, nephropathy, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, osteopathy, infection of digestive tracts with bacteria, sepsis or cancer development and progression in a patient in need thereof comprising administering to said patient a therapeutically effective amount of the pharmaceutical composition according to claim 11.

13. A method of treating or preventing nephropathy in a patient in need thereof comprising administering to said patient a therapeutically effective amount of the pharmaceutical composition according to claim 11.

14. The method according to claim 13, wherein nephropathy is diabetic nephropathy.

15. The pharmaceutical composition according to claim 7, further comprising at least one further active ingredient.

16. The pharmaceutical composition as claimed in claim 15, which comprises, as a further active ingredient, one or more antidiabetic agents, active hypoglycemic ingredients or anti-hypertension agents.

17. The pharmaceutical composition as claimed in claim 15, which comprises, as a further active ingredient, one or more beta receptor blockers, calcium channel blockers or inhibitors of the rennin-angiotensin.

18. The pharmaceutical composition as claimed in claim 17, which comprises as a further active ingredient Verapamil, Gallopamil, Fendilin, Diltiazem, Nitrendipin, Felodipin, Amlodipin, Nifedipin, Lercanidipin, Nimodipin, Nicardipin, Lacidipin, Isradipin, Nisoldipin, Nilvadipin or Manidipin.

19. The pharmaceutical composition as claimed in claim 18, which comprises as a further active ingredient Amlodipin.

20. The pharmaceutical composition as claimed in claim 15, which comprises as a further active ingredient, one or more ACE (Angiotensin Converting Enzyme) inhibitors.

21. The pharmaceutical composition as claimed in claim 20, which comprises as a further active ingredient Benazepril, Captopril, Cilazapril, Enalapril, Fosinopril, Imidapril, Lisinopril, Moexipril, Perindopril, Quinapril, Ramipril, Spirapril, Trandolapril or Zofenopril.

* * * * *